(12) United States Patent
Song

(10) Patent No.: US 8,466,199 B2
(45) Date of Patent: Jun. 18, 2013

(54) ALLYLOXY AND ALKYLOXY BENZOIC ACID DELIVERY AGENTS

(75) Inventor: Jianfeng Song, West Windsor, NJ (US)

(73) Assignee: Emisphere Technologies, Inc., Roseland, NJ (US)

( * ) Notice: Subject to any disclaimer, the term of this patent is extended or adjusted under 35 U.S.C. 154(b) by 581 days.

(21) Appl. No.: 12/529,904

(22) PCT Filed: Mar. 21, 2008

(86) PCT No.: PCT/US2008/057801
§ 371 (c)(1),
(2), (4) Date: Sep. 3, 2009

(87) PCT Pub. No.: WO2008/116141
PCT Pub. Date: Sep. 25, 2008

(65) Prior Publication Data
US 2010/0105604 A1    Apr. 29, 2010

Related U.S. Application Data

(60) Provisional application No. 60/896,188, filed on Mar. 21, 2007.

(51) Int. Cl.
*A61K 31/192*    (2006.01)

(52) U.S. Cl.
CPC ................................... *A61K 31/192* (2013.01)
USPC .......................................................... 514/568

(58) Field of Classification Search
CPC .................................................. A61K 31/192
See application file for complete search history.

(56) References Cited

U.S. PATENT DOCUMENTS

| 35,862 | A | 7/1862 | Webb |
|---|---|---|---|
| 3,160,557 | A | 12/1964 | Mauvernay |
| 3,708,522 | A | 1/1973 | LeSuer |
| 5,401,516 | A | 3/1995 | Milstein et al. |
| 5,443,841 | A | 8/1995 | Milstein et al. |
| 5,470,920 | A * | 11/1995 | Camberlin et al. ........... 525/421 |
| 5,474,978 | A | 12/1995 | Bakaysa et al. |
| 5,476,862 | A | 12/1995 | Calnek et al. |
| 5,629,020 | A | 5/1997 | Leone-Bay et al. |
| 5,643,957 | A | 7/1997 | Leone-Bay et al. |
| 5,766,633 | A | 6/1998 | Milstein et al. |
| 5,776,888 | A | 7/1998 | Leone-Bay et al. |
| 5,783,587 | A * | 7/1998 | Rogers et al. ................. 514/330 |
| 5,866,536 | A | 2/1999 | Leone-Bay et al. |
| 6,180,609 | B1 | 1/2001 | Garnick et al. |
| 6,294,186 | B1 | 9/2001 | Beerse et al. |
| 7,129,274 | B1 * | 10/2006 | Leone-Bay et al. .......... 514/571 |
| 2001/0023240 | A1 | 9/2001 | Leone-Bay et al. |
| 2002/0198364 | A1 | 12/2002 | Reeves et al. |
| 2003/0072740 | A1 | 4/2003 | Milstein et al. |
| 2003/0225300 | A1 | 12/2003 | Leone-Bay et al. |
| 2005/0002934 | A1 | 1/2005 | Reed |
| 2006/0134130 | A1 | 6/2006 | Milstein et al. |
| 2007/0141022 | A1 | 6/2007 | Milstein et al. |

FOREIGN PATENT DOCUMENTS

| WO | WO 00/22909 | * | 4/2000 |
|---|---|---|---|
| WO | 0040203 A2 | | 7/2000 |

* cited by examiner

*Primary Examiner* — Paul A Zucker
(74) *Attorney, Agent, or Firm* — Blank Rome LLP

(57) ABSTRACT

The present invention relates to pharmaceutical compounds for delivering active agents, such as biologically or chemically active agents, to a target. The invention also relates to pharmaceutical compositions comprising at least one delivery agent compound of the present invention and at least one active agent, and unit dosage forms comprising such compositions. Methods for the preparation and administration of the pharmaceutical compositions are also disclosed.

17 Claims, No Drawings

ALLYLOXY AND ALKYLOXY BENZOIC ACID DELIVERY AGENTS

CLAIM OF PRIORITY

This application is a U.S. national phase application under 35 U.S.C. §371 of International Patent Application No. PCT/US08/057801 filed Mar. 21, 2008, which claims the benefit of U.S. Provisional Application No. 60/896,188, filed Mar. 21, 2007, the disclosures of which are hereby incorporated by reference in their entireties. The International Application was published in English on Sep. 25, 2008 as WO 2008/116141.

FIELD OF THE INVENTION

The present invention relates to allyloxy and alkyloxy benzoic acid compounds (also referred to as "delivery agent" compounds), and pharmaceutically acceptable salts thereof, for delivering active agents, such as biologically or chemically active agents, to a target. The invention also relates to pharmaceutical compositions comprising at least one delivery agent compound of the present invention and at least one active agent, and unit dosage forms comprising such compositions. Methods for the preparation and administration of the pharmaceutical compositions are also disclosed.

BACKGROUND OF THE INVENTION

Conventional means for delivering active agents are often severely limited by biological, chemical and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastro-intestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Proteinoid microspheres have been used to deliver pharmaceuticals. See, for example, U.S. Pat. Nos. 5,401,516; 5,443,841; and Pat. No. Re. 35,862. In addition, certain modified amino acids have been used to deliver pharmaceuticals. See, for example, U.S. Pat. Nos. 5,629,020; 5,643,957; 5,766,633; 5,776,888; and 5,866,536.

More recently, a polymer has been conjugated to a modified amino acid or a derivative thereof via a linkage group to provide for polymeric delivery agents. The modified polymer may be any polymer, but preferred polymers include, but are not limited to, polyethylene glycol (PEG), and derivatives thereof. See, for example, International Patent Publication No. WO 00/40203.

However, there is still a need for simple, inexpensive delivery systems which are easily prepared and which can deliver a broad range of active agents by various routes.

SUMMARY OF THE INVENTION

The present invention provides compounds and compositions which facilitate the delivery of active agents. Delivery agent compounds of the present invention include those having the formula:

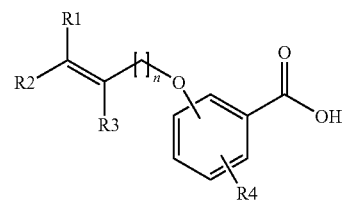

and pharmaceutically acceptable salts thereof, wherein
  n is 1, 2, 3 or 4;
  R1, R2 and R3 are independently hydrogen, methyl, or halogen; and
  R4 is hydrogen, methyl, methoxy, hydroxy, halogen, acetyl, or 2-hydroxy-ethoxy.

Delivery agent compounds of the present invention also include those having the formula:

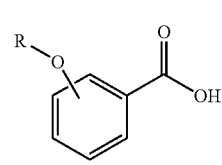

and pharmaceutically acceptable salts thereof, wherein
  R is $C_1$-$C_6$ branched or straight-chained alkyl (e.g. propyl, butyl, isopropyl, or isobutyl).

Delivery agent compounds of the present invention also include those having the formula:

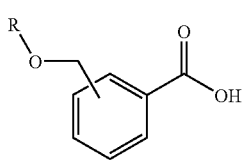

and pharmaceutically acceptable salts thereof, wherein
R is methyl, ethyl, isopropyl, propyl, butyl, allyl, 1-methylallyl, 2-methylallyl, or butenyl.

Mixtures of these delivery agent compounds may also be used.

The invention also provides a pharmaceutical composition comprising at least one delivery agent compound of the present invention, and at least one active agent (e.g., a biologically active agent). When administered with an active agent, delivery agents of the present application improve the bioavailability of the active agent compared to administration of the active agent without the delivery agent compound.

Also provided is a dosage unit form comprising a pharmaceutical composition of the present invention. The dosage unit form may be in the form of a liquid or a solid, such as a tablet, capsule or particle, including a powder or sachet.

Another embodiment is a method for administering an active agent to an animal, particularly an animal in need of the active agent, by administering a pharmaceutical composition comprising at least one of delivery agent compound of the present invention and the active agent to the animal. Preferred routes of administration include the oral, intranasal, pulmonary and intracolonic routes, particularly the oral route.

Yet another embodiment of the present invention is a method of treating a disease or for achieving a desired physiological effect in an animal (e.g., a human) by administering to the animal a pharmaceutical composition of the present invention, i.e., a pharmaceutical composition that includes at least one delivery agent compound of the present invention.

Yet another embodiment of the present invention is a method of preparing a pharmaceutical composition of the present invention by mixing at least one delivery agent compound of the present invention, and at least one active agent.

Yet another embodiment of the present invention is a method of increasing the bioavailability (e.g., the oral bioavailability) of a pharmaceutical composition containing an active agent (e.g., a biologically active agent) comprising adding a delivery agent compound of the present invention to the pharmaceutical composition.

DETAILED DESCRIPTION OF THE INVENTION

Definitions

The term "alkyl" refers to a straight-chained, branched, or substituted monovalent aliphatic hydrocarbon group containing no double or triple carbon-carbon bonds. Examples of alkyl group include, but are not limited to, methyl, ethyl, n-propyl, 1-methylethyl (isopropyl), n-butyl, n-pentyl, and 1-dimethylethyl (t-butyl).

The term "alkenyl" refers to a straight-chained, branched, or substituted monovalent aliphatic hydrocarbon group containing at least one carbon-carbon double bond. Examples of alkenyl groups include, but are not limited to, ethenyl, 1-propenyl, 2-propenyl (allyl), iso-propenyl, 2-methyl-1-propenyl, 1-butenyl, and 2-butenyl.

The term "alkynyl" refers to a straight-chained, branched or substituted monovalent hydrocarbon group having at least one carbon-carbon triple bond. Examples of alkynyl groups include, but are not limited to ethynyl, propynyl, and butnyl.

The term "alkylene" refers to a straight-chained, branched or substituted divalent aliphatic hydrocarbon group containing no double or triple bonds.

The term "alkenylene" refers to a straight-chained, branched or substituted divalent aliphatic hydrocarbon group containing at least one carbon-carbon double bond.

The term "alkynylene" refers to a straight-chained or branched divalent aliphatic hydrocarbon group containing at least one carbon-carbon triple bond.

The term "alkyloxy" refers to an alkyl group attached via an oxygen linkage to the rest of the molecule. Examples of alkyloxy groups include, but are not limited to, —$OCH_3$, and —$OC_2H_5$ groups.

The term "aryl" refers to a monovalent aromatic group, i.e. a monovalent group having one or more unsaturated carbon rings. Examples of aryl groups, include, but are not limited to, phenyl, naphthyl, tetrahydronapthyl, indanyl, and biphenyl.

The term "arylene" refers to a divalent aromatic group, i.e. a divalent group having one or more unsaturated carbon rings.

The term "alkyl(arylene)" refers to a divalent group containing an aromatic group with an alkyl group before and/or after the aromatic group.

The term "aryloxy" refers to an aryl group attached via an oxygen linkage to the rest of the molecule, such as —$OC_6H_5$.

The term "insulin" includes recombinant forms of insulin (e.g., recombinant human insulin), analogs of insulin lispro or Humalog®, as well as regular forms of insulin of human or other animal origin.

The term "heparin" includes unfractionated heparin, low molecular weight heparin, very low molecular weight heparin, of recombinant, human, or other animal origin.

The term "LHRH" or "luteinizing hormone-releasing hormone" refers to a hormone produced by the hypothalamus that signals the anterior pituitary gland to begin secreting luteinizing hormone and follicle-stimulating hormone.

The term "rhGH" refers to recombinant human growth hormone.

The term "caspofungin" or "caspofungin acetate" refers to a water-soluble, semisynthetic lipopeptide derived from the fungus, *Glarea lozoyensis*, that has activity against *Aspergillus* and *Candida* species. Caspofugin acetate (Cancidas®) has been approved by the FDA and is indicated for the treatment of invasive aspergillosis in patients who are refractory to or intolerant of other antifungal agents.

Unless otherwise specified, the term "substituted" as used herein refers to substitution with any one or any combination of the following substituents: hydroxy, $C_1$-$C_4$ alkyl, including methyl, ethyl, propyl, isopropyl, normal or iso-butyl; aryl, alkoxy, or aryloxy groups.

The term "multiply interrupted" refers to between 2 and 10 interruptions in a chain where each interruption can be independently before, after, or between any other bond along the chain and may occur in any order or combination.

The term "about" means generally means within 10%, preferably within 5%, and more preferably within 1% of a given range.

The term "short stature" refers to a subject with a size (e.g., a height) that is significantly below what is considered normal. Growth hormone, e.g., human growth hormone, is indicated for short stature.

The term "fragments" of an active agent, as used herein, refers to truncated forms of the active agent that provides, upon administration to a subject, a similar physiological effect as the non-truncated active agent. The term "analogs" of an active agent, as used herein, refers to slightly modified forms of the active agent that provides, upon administration to a subject, a similar physiological effect as the active agent from which the analog is based. It is understood that analogs of active agents (e.g., insulin analogs disclosed in U.S. Pat. No. 5,474,978) and fragments of active agents (e.g., the PTH fragments disclosed herein) can be administered with delivery agents of the present application with similar efficacy as administration of the active agent itself (e.g., insulin and PTH) with delivery agents of the present application.

Delivery Agent Compounds

Delivery agent compounds of the present invention include those compounds having the formula:

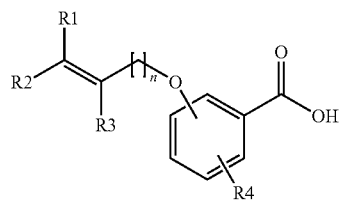

I and pharmaceutically acceptable salts thereof, wherein n is 1, 2, 3 or 4;

R1, R2 and R3 are independently hydrogen, methyl or halogen; and

R4 is hydrogen, methyl, methoxy, hydroxy, halogen, acetyl, or 2-hydroxy-ethoxy.

In another embodiment of the present invention, delivery agent compounds of the present invention include those compounds represented by Formula I above in which at least one of R1-R4 is halogen or a methyl group, or at least one of R1-R3 is a methoxy or hydroxy group.

In one embodiment of the present invention, delivery agent compounds are selected from Formula I above, in which at least one of R1-R4 is a methyl group. In another embodiment, delivery agent compounds are selected from Formula I above in which at least one of R1-R3 is a methoxy group. In another embodiment, delivery agent compounds are selected from Formula I above in which at least one of R1-R3 is a hydroxy group. In another embodiment, delivery agent compounds are selected from Formula I above in which at least one of R1-R4 is halogen, preferably at least one of R1-R4 is a chlorine atom or at least one of R1-R4 is a fluorine atom or at least one of R1-R4 is a bromine atom.

Delivery agent compounds of the present invention also include those having the formula:

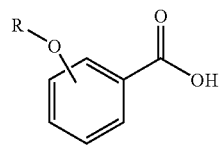

II and pharmaceutically acceptable salts thereof, wherein

R is $C_1$-$C_6$ branched or straight-chained alkyl (e.g. propyl, butyl, isopropyl, or isobutyl).

Delivery agent compounds of the present invention also include those having the formula:

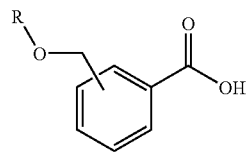

III and pharmaceutically acceptable salts thereof, wherein

R is methyl, ethyl, isopropyl, propyl, butyl, allyl, 1-methylallyl, 2-methylallyl, or butenyl.

The delivery agent compounds may be in the form of the free base or a pharmaceutically acceptable salts thereof, such as pharmaceutically acceptable acid addition salts. Suitable salts include, but are not limited to, organic and inorganic salts, for example ammonium, acetate salt, citrate salt, halide (preferably hydrochloride), hydroxide, sulfate, nitrate, phosphate, alkoxy, perchlorate, tetrafluoroborate, carboxylate, mesylate, fumerate, malonate, succinate, tartrate, acetate, gluconate, and maleate. Preferred salts include, but are not limited to, citrate and mesylate salts. The salts may also be solvates, including ethanol solvates, and hydrates.

Salts of the delivery agent compounds of the present invention may be prepared by methods known in the art. For example, citrate salts and mesylate salts may be prepared in ethanol, toluene and citric acid.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, acetonitrile, acetone, methanol, and tetrahydrofuran (THF) and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

The delivery agent may contain a polymer conjugated to it by a linkage group selected from the group consisting of —NHC(O)NH—, —C(O)NH—, —NHC(O)—, —OOC—, —COO—, —NHC(O)O—, —OC(O)NH—, —CH$_2$NH— NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly(propylene); polypropylene glycol; polyethylene glycol (PEG); and, derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

Non-limiting examples of delivery agent compounds according to the present invention include those shown below. Also included are pharmaceutically acceptable salts (e.g. the sodium salt) of the free acids below.

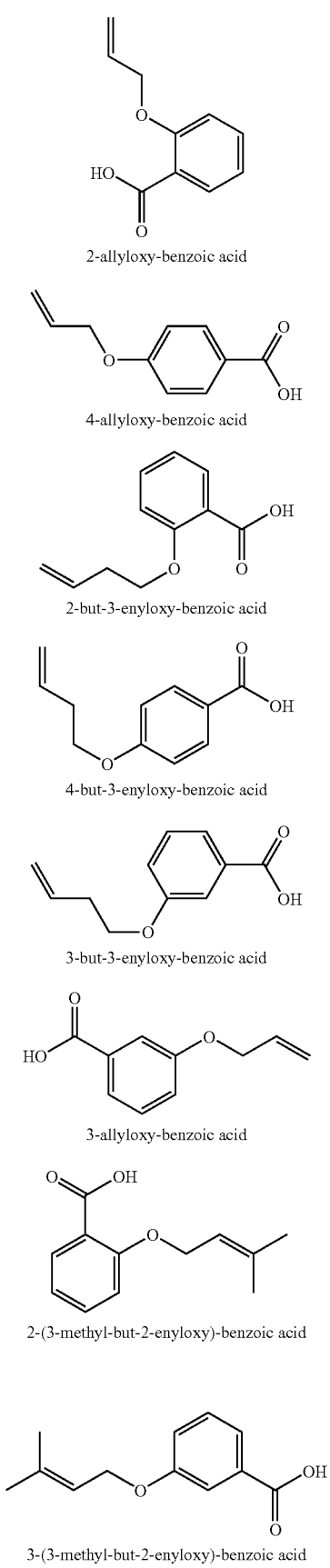

Compound 1: 2-allyloxy-benzoic acid
Compound 2: 4-allyloxy-benzoic acid
Compound 3: 2-but-3-enyloxy-benzoic acid
Compound 4: 4-but-3-enyloxy-benzoic acid
Compound 5: 3-but-3-enyloxy-benzoic acid
Compound 6: 3-allyloxy-benzoic acid
Compound 7: 2-(3-methyl-but-2-enyloxy)-benzoic acid
Compound 8: 3-(3-methyl-but-2-enyloxy)-benzoic acid
Compound 9: 4-(3-methyl-but-2-enyloxy)-benzoic acid
Compound 10: 2-allyloxy-5-methoxy-benzoic acid
Compound 11: 2-allyloxy-4-methoxy-benzoic acid
Compound 12: 2-allyloxy-3-methoxy-benzoic acid
Compound 13: 2-allyloxy-5-methyl-benzoic acid
Compound 14: 2-allyloxy-6-methyl-benzoic acid

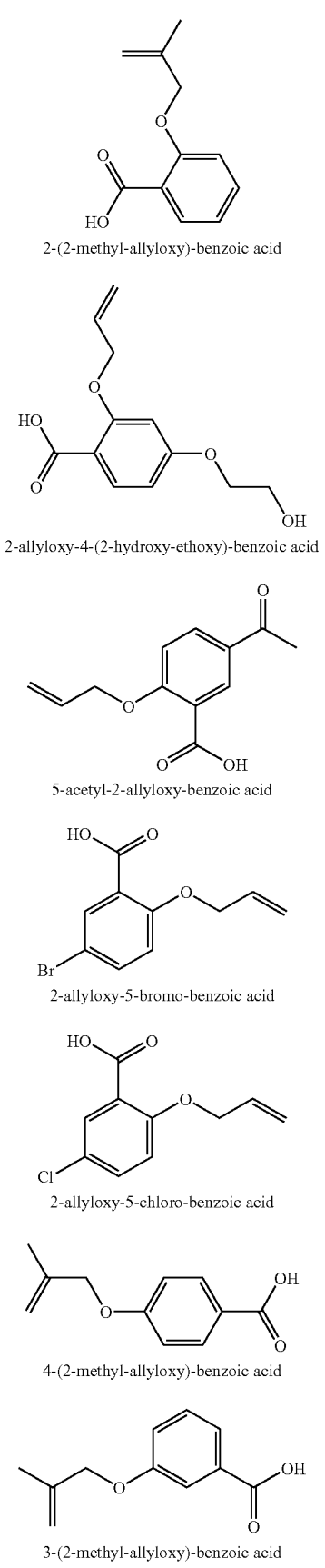

Compound 15
2-(2-methyl-allyloxy)-benzoic acid

Compound 16
2-allyloxy-4-(2-hydroxy-ethoxy)-benzoic acid

Compound 17
5-acetyl-2-allyloxy-benzoic acid

Compound 18
2-allyloxy-5-bromo-benzoic acid 2-allyloxy-5-chloro-benzoic acid

Compound 20
4-(2-methyl-allyloxy)-benzoic acid

Compound 21
3-(2-methyl-allyloxy)-benzoic acid

Compound 22
3-allyloxy-4-methoxy-benzoic acid

Compound 23
4-methoxy-3-(2-methyl-allyloxy)-benzoic acid

Compound 24
3-propoxy-benzoic acid

Compound 25
4-propoxy-benzoic acid

Compound 26
3-butoxy-benzoic acid

Compound 27
2-propoxy-benzoic acid

-continued

Compound 28

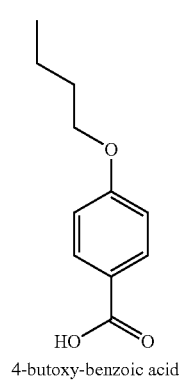
4-butoxy-benzoic acid

Compound 29

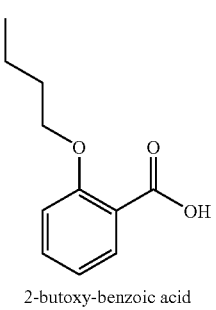
2-butoxy-benzoic acid

Compound 30

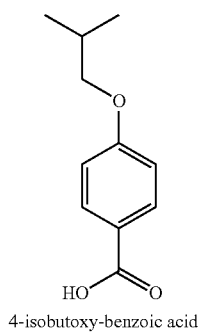
4-isobutoxy-benzoic acid

Compound 31

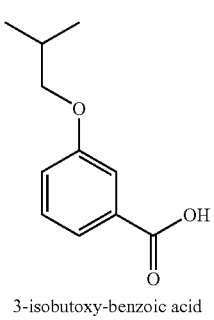
3-isobutoxy-benzoic acid

Compound 32

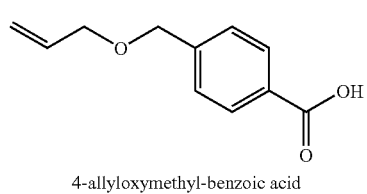
4-allyloxymethyl-benzoic acid

-continued

Compound 33

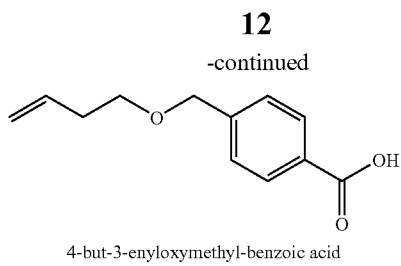
4-but-3-enyloxymethyl-benzoic acid

Compound 34

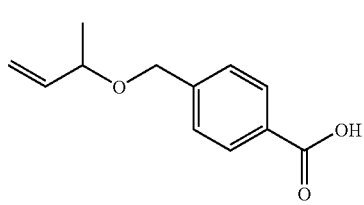
4-(1-methyl-allyloxymethyl)-benzoic acid

Compound 35

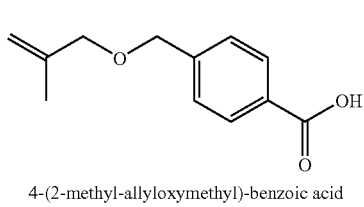
4-(2-methyl-allyloxymethyl)-benzoic acid

Compound 36

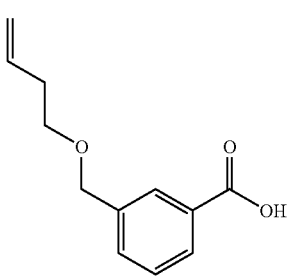
3-but-3-enyloxymethyl-benzoic acid

Compound 37

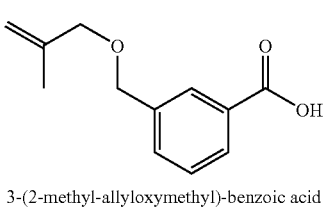
3-(2-methyl-allyloxymethyl)-benzoic acid

Compound 38

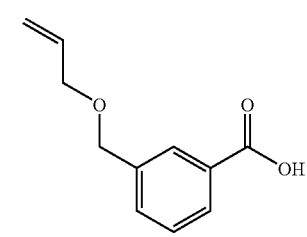
3-allyloxymethyl-benzoic acid

Compound 39

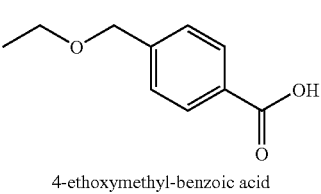
4-ethoxymethyl-benzoic acid

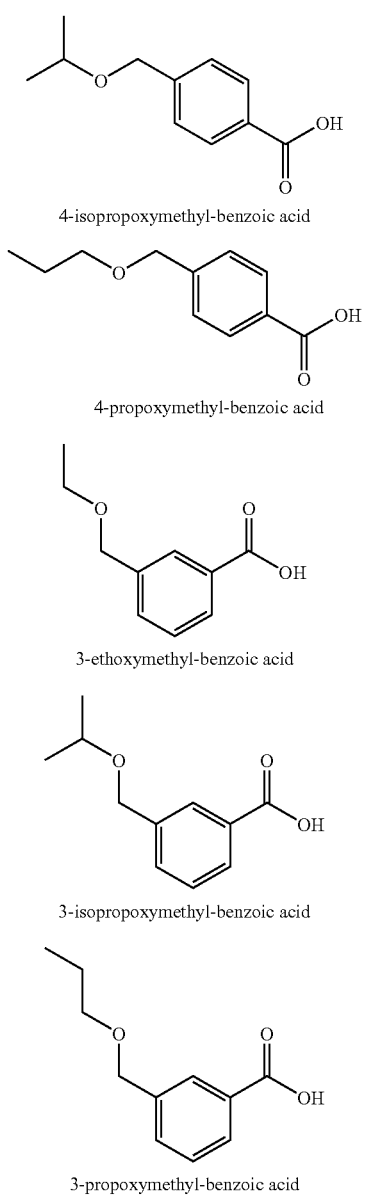

Compound 40
4-isopropoxymethyl-benzoic acid

Compound 41
4-propoxymethyl-benzoic acid

Compound 42
3-ethoxymethyl-benzoic acid

Compound 43
3-isopropoxymethyl-benzoic acid

Compound 44
3-propoxymethyl-benzoic acid

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastro-intestinal tract by acid hydrolysis, enzymes and the like. Also included as suitable active agents are those macromolecular agents whose physiochemical characteristics, such as, size, structure or charge, prohibit or impede absorption when dosed orally.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e., polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including α-interferon (e.g., interferon alfacon-1 (available as Infergen® from Inter-Mune, Inc. of Brisbane, Calif.)), β-interferon and γ-interferon; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; anti-migraine agents such as sumatriptan, almotriptan, naratriptan, rizatriptan, frovatriptan, eletriptan, BIBN-4096BS and other calcitonin gene-related proteins antagonists; glucagon-like peptide 1 (GLP-1); Argatroban; glucagon; caspofungin acetate; antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof.

Delivery Systems

The pharmaceutical composition of the present invention comprises one or more delivery agent compounds of the present invention, and one or more active agents (e.g., biologically active agents). In one embodiment, one or more of the delivery agent compounds, or salts of these compounds, may be used as a delivery agent by mixing delivery agent compounds with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

Alternatively, the delivery agent compound and active agent can be separately administered in sequential fashion.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitors.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

Generally, the amount of delivery agent compound in the composition is an amount effective to facilitate delivery of the active agent. The total amount of active agent and delivery agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects. Generally, the weight ratio of delivery agent to active agent ranges from about 1000:1 or 800:1 to about 10:1 or 1:10, and preferably ranges from about 400:1 or 200:1 to about 100:1 or 25:1. Other ranges are contemplated to be within acceptable ranges for delivery of some active compounds, such as from about 100:1 or 50:1 to about 5:1 or 2.5:1, or from about 60:1 or 30:1 to about 1:1 or 0.5:1. Such ranges and ratios can be determined by one skilled in the art.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e., the area in which the active agent of the delivery composition is to be released) and within the body of the animal to which they are administered. Particularly, the compounds and compositions of the present invention are useful for orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering the active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as any one of the diseases or conditions listed in the table below, in an animal by administering the composition of the present invention. Preferably, an effective amount of the composition for the treatment or prevention of the desired disease or for achieving the desired physiological effect is administered. Specific indications for active agents can be found in the *The Physicians' Desk Reference* (58$^{th}$ Ed., 2004, Medical Economics Company, Inc., Montvale, N.J.), and Fauci, A S, et. al., *Harrison's Principles of Internal Medicine* (14$^{th}$ Ed., 1998, McGraw-Hill Health Professions Division, New York. Both of these references are herein incorporated by reference in their entirety. The active agents in the table below include their analogs, fragments, mimetics, and polyethylene glycol-modified derivatives (e.g., the PEGylated derivative of granulocyte colony stimulating factor sold as Neulasta®).

| Active Agent | Disease and Physiological Effect |
| --- | --- |
| Growth hormones (including human recombinant growth hormone and growth-hormone releasing factors and its analogs) | Growth disorders |
| Interferons, including α, β and γ | Viral infection, including chronic cancer, hepatitis, and multiple sclerosis |
| Interleukins (e.g., Interleukin-1; interleukin-2) | Viral infection; cancer; cell mediated immunity; and transplant rejection |

-continued

| Active Agent | Disease and Physiological Effect |
|---|---|
| Insulin; Insulin-like growth factor IGF-1 | Diabetes |
| Immune Globulins, such as IVIg | smallpox, rabies, and diphtheria, Alzheimer's Disease; Primary immunodeficiencies; Acute Guillain-Barré syndrome; Chronic idiopathic demyelinating polyneuropathy (CIDP); Myasthenia gravis, polymyositis, and dermatomyositis; neonatal immune thrombocytopenia, heparin-induced thrombocytopenia, and antiphospholipid antibody syndrome; Posttransfusion purpura |
| Heparin, including Lovenox ® | Treatment and Prevention of Thrombosis, including (Deep Vein Thrombosis); prevention of blood coagulation |
| Calcitonin | Osteoporosis; diseases of the bone; bone pain; analgesic (including pain associated with osteoporosis or cancer) |
| Erythropoietin, Pegylated erythropoietin | Anemia; HIV/HIV-therapy Associated Anemia; Chemotherapeutically-Induced Anemia |
| Atrial naturetic factor | Vasodilation |
| Antigens | Infection |
| CPHPC | Reduction of amyloid deposits and systemic amyloidoisis often (but not always) in connection with Alzheimer's disease, Type II diabetes, and other amyloid-based diseases |
| Monoclonal antibodies | To prevent graft rejection; cancer; used in assays to detect diseases |
| Somatostatin/octreotide | Bleeding ulcer; erosive gastritis; variceal bleeding; diarrhea; acromegaly; TSH-secreting pituitary adenomas; secretory pancreatic tumors; carcinoid syndrome; reduce proptosis/thyroid-associated ophthalmopathy; reduce macular edema/retinopathy |
| Protease inhibitors | HIV Infection/AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; Leutinizing Hormone; follicle stimulating hormone | Regulate reproductive function |
| Glucocerebrosidase | Gaucher disease (to metabolize lipoprotein) |
| Thrombopoietin | Thrombocytopenia |
| Filgrastim (Granulocyte Colony Stimulating Factor); GM-CSF, (sargramostim) and their Pegylated forms | shorten the duration of chemotherapy-induced neutropenia and thus treat or prevent infection in chemotherapy patients; Inhibit the growth of or to kill *Mycobacterium* Intracellular *Avium* Infection (MAC) |
| RNAi | Huntington, Alzheimers, Viral Infections (HIV, Hepatitis A, B or C, RSV), Cancers; Macular Degeneration |
| Prostaglandins | Hypertension |
| Cyclosporin | Transplant rejection; psoriasis, inflammatory alopecias; Sjogren's syndrome; Keratoconjunctivitis Sicca |
| Vasopressin | Nocturnal Enuresis; antidiuretic |
| Cromolyn sodium; | Asthma; allergies |
| Vancomycin | Treat or prevent antimicrobial-induced infections including, but not limitted to methacillin-resistant *Staphalococcus aureus* and *Staph. epidermiditis* |
| gallium salts (such as gallium nitrate) | Osteoporosis; Paget's disease; Inhibits osteoclasts; Promotes osteoblastic activity, hypercalcemia, including cancer related hypercalcemia, urethral (urinary tract) malignancies; anti-tumors, cancers, including urethral and bladder cancers; lymphoma; malignancies (including bladder cancer); leukemia; management of bone metastases (and associated pain); muliple myeloma, attenuate immune response, including allogenic transplant rejections; disrupt iron metabolism; promote cell migration; wound repair; to attenuate or treat infectious processes of *mycobacterium* species, including but not limited to *mycobacterium tubercolosis*, and *mycobacterium avium* complex |
| Desferrioxamine (DFO) | Iron overload |
| Parathyroid hormone (PTH), including its fragments | Osteoporosis; Diseases of the bone |

-continued

| Active Agent | Disease and Physiological Effect |
|---|---|
| Antimicrobials | Infection including but not limited to gram-positive bacterial infection |
| Vitamins | Treat and prevent Vitamin deficiencies |
| Bisphosphonates | Osteoporosis; Paget's disease; bone tumors and metastases (and associated pain); Breast cancer; including as adjuvant therapy for early stage breast cancer; management of bone metastases (and associated pain), including bone metastases associate with breast cancer, prostate cancer, and lung cancer; Inhibits osteoclasts; Promotes osteoblastic activity; treat and/or prevent bone mineral density (bmd) loss; multiple myeloma; prevention of bone complications related to malignant osteolysis; fibrous dysplasia; pediatric osteogenesis imperfecta; hypercalcemia, urethral (urinary tract) malignancies; reflex sympathetic dystropy synodrome, acute back pain after vertebral crush fracture, chronic inflammatory joint disease, renal bone disease, extrosseous calcifications, analgesic, vitamin D intoxication, periarticular ossifications |
| BIBN4096BS —(1-Piperidinecarboxamide. N-[2-[[5-amino-1-[[4-(4-pyridinyl)-1-piperazinyl)carbonyl]pentyl]amino]-1-[(3,5-dibromo-4-hydroxyphenyl)methyl]-2-oxoethyl]-4(1,4-dihydro-2-oxo-3(2H0-quinazolinyl)-.[R—(R*,S*)]-) | Anti-migraine; calcitonin gene-related peptide antagonist |
| Glucagon | improving glycemic control (e.g. treating hypoglycemia and controlling hypoglycemic reactions), obesity; a diagnostic aid in the radiogical examination of the stomach, duodenum, small bowel and colon; Treat acute poisoning With Cardiovascular Agents including, but not limited to, calcium channel blockers, beta blockers |
| GLP-1, Exendin-3, Exendin-4, Obestatin | Diabetes; improving glycemic control (e.g. treating hypoglycemia and controlling hypoglycemic reactions), obesity |
| dipeptidyl peptidase IV (DPP-4) inhibitors | Diabetes; improving glycemic control (e.g. treating hypoglycemia), obesity |
| acyclovir | Used to treat herpes infections of the skin, lip and genitals; herpes zoster (shingles); and chickenpox |
| HIV Entry Inhibitors (e.g. Fuzeon) | Inhibit entry of HIV into host cells |
| sumatriptin, almotriptan, naratriptan, rizatriptan, frovatriptan and eletriptan (piperidinyloxy)phenyl, (piperidinyloxy)pyridinyl, (piperidinylsulfanyl)phenyl and (piperidinylsulfanyl)pyridinyl compounds | anti-migraine serotonin agonists |
| Neuraminidase inhibitors: peramivir, zanamivir, oseltamivir, BCX-1898, BCX-1827, BCX-1989, BCX 1923, BCX 1827 and A315675; M2 inhibitors: amantadine, rimantadine; Nucleoside/Nucleotide Reverse Transcriptase Inhibitors, Non-nucleoside Reverse Transcriptase Inhibitors, Protease Inhibitors, Fusion inhibitors: thiovir, thiophosphonoformate, foscarnet, enfuviritide, zidovudine, didanosine, zalcitabine, stavudine, lamivudine, emtricitabine, abacavir, azidothymidine, tenofovir disoproxil, delavridine, efavirenz, nevirapine, ritonavir, nelfinavir mesylate, saquinvir mesylate, indinavir sulfate, amprenavir, lopinavir, lopinavir, fosamprenavir calcium, atazanavir sulfate | Antivirals |
| Peptide YY (PYY) and PYY-like Peptides (e.g. PYY[3-36]) | Obesity, Diabetes, Eating Disorders, Insulin-Resistance Syndromes |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into the circulation. The bioavailability of the agent can be readily assessed by measuring a known pharmacological activity in blood, e.g., an increase in blood clotting time caused by heparin, or a decrease in circulating calcium levels caused by calcitonin. Alternatively, the circulating levels of the active agent itself can be measured directly.

One embodiment of the present invention provides a pharmaceutical composition comprising an effective amount of insulin and an effective amount of at least one of the delivery agents described herein. For example, one embodiment of the present invention provides a pharmaceutical composition comprising about 0.1 to 2.0 mg/kg (e.g., 0.5 mg/kg) of insulin and about 50 to 800 mg/kg (e.g., 200 mg/kg) of any one of the delivery agent compounds of the present invention.

Yet another embodiment is a method of treating diseases characterized by hyperglycemia, such as diabetes, comprising administering a pharmaceutical composition of the present invention to a subject.

One embodiment of the present invention provides a pharmaceutical composition comprising an effective amount of heparin and an effective amount of at least one of the delivery agents described herein. For example, one embodiment of the present invention provides a pharmaceutical composition comprising about 5 to 125 mg/kg (e.g., 25 mg/kg or 80 mg/kg) of heparin and about 5 to 500 mg/kg (e.g., 50 mg/kg or 200 mg/kg) of any one of the delivery agent compounds of the present invention.

Yet another embodiment is a method of treating or preventing disease characterized by intravascular thrombi by administering an effective amount of heparin and an effective amount of at least one delivery agent of the present invention to a subject.

Yet another embodiment is a method of preventing DVT in susceptible individuals by administering an effective amount of heparin and an effective amount of at least one delivery agent compound of the present invention to a subject.

One embodiment of the present invention provides a pharmaceutical composition comprising an effective amount of rhGH and an effective amount of at least one of the delivery agents described herein. For example, one embodiment of the present invention provides a pharmaceutical composition comprising about 0.25 to 10 mg/kg (e.g., 3 mg/kg) of rhGH and about 50 to 500 mg/kg (e.g., 200 mg/kg) of any one of the delivery agent compounds of the present invention.

Yet another embodiment is a method of treating or preventing short stature by administering an effective amount of rhGH and an effective amount of at least one delivery agent compound of the present invention to a subject.

Yet another embodiment is a method of treating or preventing a disease which requires supplementation of growth hormone by administering an effective amount of at least one delivery agent compound of the present invention to a subject.

One embodiment of the present invention provides a pharmaceutical composition comprising an effective amount of LHRH and an effective amount of at least one of the delivery agents described herein. For example, one embodiment of the present invention provides a pharmaceutical composition comprising about 0.1 to 10 mg/kg (e.g., 1 mg/kg) of LHRH and about 50 to 500 mg/kg (e.g., 200 mg/kg) of any one of the delivery agent compounds of the present invention.

Yet another embodiment is a method of treating or preventing infertility in men or women which requires supplementation of LHRH by administering an effective amount of LHRH and an effective amount of at least one delivery agent of the present invention to a subject.

Yet another embodiment is a method of treating or preventing a disease which requires supplementation of LHRH by administering an effective amount of LHRH and an effective amount of at least one delivery agent of the present invention to a subject.

One embodiment of the present invention provides a pharmaceutical composition comprising an effective amount of caspofungin acetate (e.g., Cancidas®) and an effective amount of at least one of the delivery agents described herein. For example, one embodiment of the present invention provides a pharmaceutical composition comprising about 5 to 125 mg/kg (e.g., 25 mg/kg) of caspofungin acetate and about 50 to 500 mg/kg (e.g., 200 mg/kg) of any one of the delivery agent compounds of the present invention.

Yet another embodiment is a method of treating or preventing candidiasis or other systemic or localized fungal infections by administering an effective amount of caspofungin acetate and an effective amount of at least one delivery agent of the present invention to the subject.

EXAMPLES

The following examples illustrate the present invention without limitation.

Example 1

The compounds of Formula I are synthesized according to Scheme 1 below by the coupling reaction of the corresponding hydroxy-benzoate and alkenyl bromide. R1, R2, R3, R4 and n are as defined above. R5 is an alkyl group.

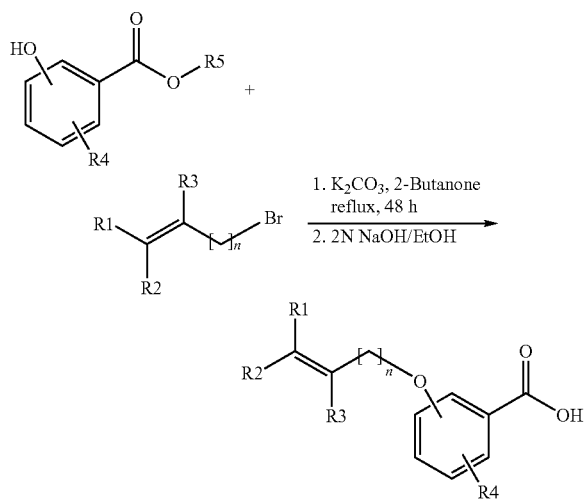

Example 2

Preparation of 2-Allyloxy-benzoic acid
(Compound 1)

Under $N_2$, the mixture of ethyl salicylate (16.62 g, 100 mmol), allyl bromide (18.15 g, 12.7 ml, 150 mmol) and potassium carbonate (17.97 g, 130 mmol) in dry 2-butanone (400 ml) was heated to reflux for 48 h. After the reaction mixture cooled down to 25° C., the suspended inorganic salt was removed by filtration. The concentration of the resulting solution by rotary evaporation yielded pale yellowish syrup, which was then mixed with 2N NaOH (80 ml, 160 mmol) and EtOH (150 ml). After this mixture was stirred for 2 h at 50° C., ethanol was removed at reduced pressure. The aqueous solution was acidified by 6N HCl to pH 2 at 5° C. to generate white precipitate, which was then collected by filtration. The recrystallization of this crude product from hexane/ether yielded pure 2-Allyloxy-benzoic acid as colorless crystal (14.87 g, 83.5%). Microanalysis Calc. for $C_{10}H_{10}O_3$ (178.19): C 67.41, H 5.66; found: C 67.35, H 5.39. $^1$H-NMR (400 MHz, d6-DMSO): 12.51 (s, —$CO_2$H); 7.55 (m, 1 arom. H); 7.38 (m, 1 arom. H); 7.01 (m, 1 arom. H); 6.90 (m, 1 arom. H); 5.93 (m, —CH=$CH_2$); 5.40, 5.15 (2 d-like, —CH=$CH_2$); 4.57 (d-like, $CH_2$—CH=$CH_2$). $^{13}$C-NMR (100 MHz, d6-DMSO): 167.35 (—C=O); 156.88; 133.36; 132.81; 130.62; 121.68; 120.16; 116.91; 113.64; 68.52.

Example 3

Preparation of 4-Allyloxy-benzoic acid
(Compound 2)

The reaction of ethyl 4-hydroxybenzoate and allyl bromide in 2-butanone in the presence of potassium carbonate was performed as described in Example 2 to give 4-Allyloxy-benzoic acid as white powder. $^1$H-NMR (400 MHz, d6-DMSO): 12.56 (s, —$CO_2$H); 7.83 (d-like, J=8.0, 2 arom. H); 6.97 (d-like, J=8.0, 2 arom. H); 5.99 (m, —CH=$CH_2$); 5.38, 5.24 (2 d-like, —CH=$CH_2$); 4.59 (d-like, $CH_2$—CH=$CH_2$); $^{13}$C-NMR (100 MHz, d6-DMSO): 166.92 (—C=O); 161.72; 133.17; 131.28 (2 arom. C); 123.04; 117.80; 114.42 (2 arom. C); 68.34.

Example 4

Preparation of 2-But-3-enyloxy-benzoic acid
(Compound 3)

The reaction of ethyl salicylate and 4-bromo-1-butene in 2-butanone in the presence of potassium carbonate was performed as described in Example 2 to give 2-But-3-enyloxy-benzoic acid as white powder. $^1$H-NMR (400 MHz, d6-DMSO): 12.57 (s, —$CO_2$H); 7.63 (m, 1 arom. H); 7.46 (m, 1 arom. H); 7.12 (m, 1 arom. H); 6.99 (m, 1 arom. H); 5.92 (m, —CH=$CH_2$); 5.18, 5.08 (2 d-like, —CH=$CH_2$); 4.07 (t, J=6.4, $OCH_2$—$CH_2$—CH=$CH_2$); 2.49 (m, $OCH_2$—$CH_2$—CH=$CH_2$). $^{13}$C-NMR (100 MHz, d6-DMSO): 167.33 (—C=O); 157.18; 134.77; 132.85; 130.52; 121.75; 120.16; 117.01; 113.60; 67.70; 33.20.

Example 5

Preparation of 4-But-3-enyloxy-benzoic acid
(Compound 4)

The reaction of ethyl 4-hydroxybenzoate and 4-bromo-1-butene in 2-butanone in the presence of potassium carbonate was performed as described in Example 2 to give 4-But-3-enyloxy-benzoic acid as white powder. $^1$H-NMR (400 MHz, d6-DMSO): 12.57 (s, —$CO_2$H); 7.89 (d, J=6.9, 2 arom. H); 7.00 (d, J=6.9, 2 arom. H); 5.86 (m, —CH=$CH_2$); 5.19, 5.08 (2 d-like, CH=$CH_2$); 4.00 (t, J=6.6, $OCH_2$—$CH_2$—CH=$CH_2$); 2.50 (m, $OCH_2$—$CH_2$—CH=$CH_2$). $^{13}$C-NMR (100 MHz, d6-DMSO): 166.95 (—C=O); 162.08; 134.66; 131.32 (2 arom. C); 122.92; 117.14; 114.22 (2 arom. C); 66.92; 32.90.

Example 6

Preparation of 3-But-3-enyloxy-benzoic acid
(Compound 5)

The reaction of ethyl 3-hydroxybenzoate and 4-bromo-1-butene in 2-butanone in the presence of potassium carbonate was performed as described in Example 2 to give 3-But-3-enyloxy-benzoic acid as white powder. $^1$H-NMR (400 MHz, d6-DMSO): 12.96 (s, —$CO_2$H); 7.48 (d-like, 1 arom. H); 7.40 (m, 2 arom. H); 7.18 (m, 1 arom. H); 5.86 (m, —CH=$CH_2$); 5.15, 5.08 (2 d-like, CH=$CH_2$); 4.03 (t, J=6.6, $OCH_2$—$CH_2$—CH=$CH_2$); 2.47 (m, $OCH_2$—$CH_2$—CH=$CH_2$). $^{13}$C-NMR (100 MHz, d6-DMSO): 167.07 (—C=O); 158.44; 134.79; 132.18; 129.70; 121.55; 119.31; 117.04; 114.54; 66.84; 32.90.

Example 7

Preparation of 3-Allyloxy-benzoic acid
(Compound 6)

The reaction of ethyl 3-hydroxybenzoate and allyl bromide in 2-butanone in the presence of potassium carbonate was performed as described in Example 2 to give 3-Allyloxy-benzoic acid as white powder. $^1$H-NMR (400 MHz, d6-DMSO): 12.97 (s, —$CO_2$H); 7.47 (d-like, 1 arom. H); 7.40 (m, 2 arom. H); 7.18 (m, 1 arom. H); 5.99 (m, —CH=$CH_2$); 5.37, 5.23 (2 d-like, CH=$CH_2$); 4.03 (d-like, $CH_2$—CH_$CH_2$). $^{13}$C-NMR (100 MHz, d6-DMSO): 167.08 (C=O); 158.12; 133.44; 132.27; 129.67; 121.66; 119.47; 117.47; 114.78; 68.27.

Example 8

Preparation of 2-(3-Methyl-but-2-enyloxy)-benzoic acid (Compound 7)

The reaction of ethyl salicylate and 3,3-dimethylallyl bromide in 2-butanone in the presence of potassium carbonate was performed as described in Example 2 to give 2-(3-Methyl-but-2-enyloxy)-benzoic acid as white powder. $^1$H-NMR (400 MHz, d6-DMSO): 12.50 (s, —$CO_2$H); 7.55 (m, 1 arom. H); 7.41 (m, 1 arom. H); 7.07 (m, 1 arom. H); 6.92 (m, 1 arom. H); 5.36 (m, CH=C$(CH_3)_2$); 4.54 (d-like, $CH_2$CH=C$(CH_3)_2$); 1.72, 1.68 (2s, CH=C$(CH_3)_2$). $^{13}$C-NMR (100 MHz, d6-DMSO): 167.42 (C=O); 157.06; 136.97; 132.70; 130.44; 121.91; 119.99; 119.82; 113.79; 65.23; 25.42; 18.03.

Example 9

Preparation of 3-(3-Methyl-but-2-enyloxy)-benzoic acid (Compound 8)

The reaction of ethyl 3-hydroxybenzoate and 3,3-dimethylallyl bromide in 2-butanone in the presence of potassium carbonate was performed as described in Example 2 to give 3-(3-Methyl-but-2-enyloxy)-benzoic acid as white powder. $^1$H-NMR (400 MHz, d6-DMSO): 12.97 (br, —$CO_2$H); 7.48 (m, 1 arom.H); 7.42 (m, 1 arom.H); 7.41 (m, 1 arom.H); 7.15 (m, 1 arom.H); 5.40 (m, CH=C$(CH_3)_2$); 4.54 (d-like, $CH_2$CH=C$(CH_3)_2$); 1.69, 1.63 (2s, CH=C$(CH_3)_2$). $^{13}$C-

NMR (100 MHz, d6-DMSO): 167.16 (C=O); 158.38; 137.32; 132.24; 129.59; 121.43; 119.68; 119.48; 114.67; 64.46; 25.40; 18.00.

Example 10

Preparation of 4-(3-Methyl-but-2-enyloxy)-benzoic acid (Compound 9)

The reaction of ethyl 4-hydroxybenzoate and 3,3-dimethylallyl bromide in 2-butanone in the presence of potassium carbonate was performed as described in Example 2 to give 4-(3-Methyl-but-2-enyloxy)-benzoic acid as white powder. $^1$H-NMR (400 MHz, d6-DMSO): 12.54 (s, —CO$_2$H); 7.81 (d-like, 2 arom.H); 6.95 (d-like, 2 arom.H); 5.38 (m, CH=C(CH$_3$)$_2$); 4.54 (d-like, CH$_2$CH=C(CH$_3$)$_2$); 1.69, 1.64 (2s, CH=C(CH$_3$)$_2$). $^{13}$C-NMR (100 MHz, d6-DMSO): 166.96 (C=O); 162.05; 137.66; 131.25 (2 arom. C); 122.78; 119.38; 114.36 (2 arom.C); 64.58; 25.37; 17.99.

Example 11

Preparation of 2-Allyloxy-5-methoxy-benzoic acid (Compound 10)

The reaction of methyl 2-hydroxy-5-methoxy-benzoate and allyl bromide in 2-butanone in the presence of potassium carbonate was performed as described in Example 2 to give 2-Allyloxy-5-methoxy-benzoic acid as white powder. $^1$H-NMR (400 MHz, d6-DMSO): 12.65 (br, —CO$_2$H); 7.11 (m, 1 arom.H); 7.00 (m, 2 arom.H); 5.95 (m, —CH=CH$_2$); 5.39, 5.17 (2 d-like, CH=CH$_2$); 4.49 (d-like, CH$_2$—CH=CH$_2$); 3.68 (s, OCH$_3$). $^{13}$C-NMR (100 MHz, d6-DMSO): 167.06 (C=O); 152.69; 150.99; 133.70; 122.54; 118.27; 116.84; 115.76; 115.08; 69.50; 55.49.

Example 12

Preparation of 2-Allyloxy-4-methoxy-benzoic acid (Compound 11)

The reaction of methyl 2-hydroxy-4-methoxy-benzoate and allyl bromide in 2-butanone in the presence of potassium carbonate was performed as described in Example 2 to give 2-Allyloxy-4-methoxy-benzoic acid as white powder. $^1$H-NMR (400 MHz, d6-DMSO): 12.18 (s, —CO$_2$H); 7.70 (m, 1 arom. H); 6.58 (m, 2 arom. H); 6.01 (m, —CH=CH$_2$); 5.51, 5.24 (2 d-like, CH=CH$_2$); 4.62 (d-like, CH$_2$—CH=CH$_2$); 3.81 (s, OCH$_3$). $^{13}$C-NMR (100 MHz, d6-DMSO): 166.45 (C=O); 163.45; 159.40; 133.25; 133.22; 116.91; 112.98; 105.37; 100.01; 68.63; 55.45.

Example 13

Preparation of 2-Allyloxy-3-methoxy-benzoic acid (Compound 12)

The reaction of methyl 2-hydroxy-3-methoxy-benzoate and allyl bromide in 2-butanone in the presence of potassium carbonate was performed as described in Example 2 to give 2-Allyloxy-3-methoxy-benzoic acid as white powder. $^1$H-NMR (400 MHz, d6-DMSO): 12.18 (s, —CO$_2$H); 7.10 (m, 3 arom. H); 5.97 (m, —CH=CH$_2$); 5.28, 5.14 (2 d-like, CH=CH$_2$); 4.43 (d-like, CH$_2$—CH=CH$_2$); 3.77 (s, OCH$_3$). $^{13}$C-NMR (100 MHz, d6-DMSO): 167.42 (C=O); 153.06; 146.24; 134.49; 127.66; 123.94; 121.07; 117.10; 115.57; 73.88; 55.93.

Example 14

Preparation of 2-Allyloxy-5-methyl-benzoic acid (Compound 13)

The reaction of ethyl 2-hydroxy-5-methyl-benzoate and allyl bromide in 2-butanone in the presence of potassium carbonate was performed as described in Example 2 to give 2-Allyloxy-5-methyl-benzoic acid as white powder. $^1$H-NMR (400 MHz, d6-DMSO): 12.52 (s, —CO$_2$H); 7.43 (m, 1 arom. H); 7.26 (m, 1 arom. H); 6.98 (m, 1 arom. H); 5.99 (m, —CH=CH$_2$); 5.46, 5.22 (2 d-like, CH=CH$_2$); 4.56 (d-like, CH$_2$—CH=CH$_2$); 2.23 (s, —CH$_3$). $^{13}$C-NMR (100 MHz, d6-DMSO): 167.39 (C=O); 154.91; 133.52; 133.20; 130.91; 129.05; 121.34; 116.83; 113.79; 68.69; 19.78.

Example 15

Preparation of 2-Allyloxy-6-methyl-benzoic acid (Compound 14)

Under N$_2$, the mixture of ethyl 2-hydroxy-6-methyl-benzoate (5.00 g, 27.75 mmol), allyl bromide (5.08 g, 3.55 ml, 42.00 mmol) and potassium carbonate (4.42 g, 32.00 mmol) in dry 2-Butanone (100 ml) was heated to reflux for 48 h. After the reaction mixture cooled down to 25° C., the suspended inorganic salt was removed by filtration. The concentration of the resulting solution by rotary evaporation yielded pale yellowish syrup, which was then mixed with 2N NaOH (20 ml, 40 mmol) and EtOH (30 ml). After this mixture was stirred for 48 h at 80° C., ethanol was removed at reduced pressure. After the aqueous solution was acidified by 6N HCl to pH 2 at 5° C., the mixture was extracted with Et$_2$O (50 ml×3). The organic phase was combined and washed with water (10 ml×2) respectively. The ether extract was dried with anhydrous sodium sulfate and then concentrated to give 2-Allyloxy-6-methyl-benzoic acid as oil (4.44 g, 23.10 mmol). The title compound was then treated with of 1M sodium trimethylsilanolate (21.0 ml, 21.0 mmol) to give sodium 2-allyloxy-6-methyl-benzoate (4.65 g) as white powder. $^1$H-NMR (400 MHz, D$_2$O): 7.06 (m, 1 arom. H); 6.73 (m, 2 arom. H); 5.92 (m, —CH=CH$_2$); 5.29, 5.14 (2 d-like, CH=CH$_2$); 4.47 (d-like, CH$_2$—CH=CH$_2$); 2.10 (s, —CH$_3$). $^{13}$C-NMR (100 MHz, D$_2$O): 176.86 (CO);=153.10; 134.09; 133.61; 131.33; 127.99; 122.84; 117.22; 110.91; 69.60; 18.36.

Example 16

Preparation of 2-(2-Methyl-allyloxy)-benzoic acid (Compound 15)

Under N$_2$, the mixture of ethyl salicylate (4.99 g, 4.40 ml, 30.0 mmol), 3-Bromo-2-methyl-propene (8.10 g, 6.1 ml, 60.00 mmol) and potassium carbonate (5.53 g, 40.0 mmol) in dry 2-Butanone (120 ml) was heated to reflux for 48 h. After the reaction mixture cooled down to 25° C., the suspended inorganic salt was removed by filtration. The concentration of the resulting solution by rotary evaporation yielded pale yellowish syrup, which was then mixed with 2N NaOH (23 ml, 46 mmol) and EtOH (30 ml). After this mixture was stirred for 2 h at 50° C., ethanol was removed at reduced pressure. After the aqueous solution was acidified by 6N HCl to pH 2 at 5° C., the mixture was extracted with Et$_2$O (50 ml×3). The organic phase was combined and washed with water (10 ml×2) respectively. The ether extract was dried with anhydrous sodium sulfate and then concentrated to give 2-(2-Methylallyloxy)-benzoic acid as oil (5.26 g, 27.36 mmol). The title compound was then treated with of 1M sodium trimethylsilanolate (24.5 ml, 24.5 mmol) to give sodium 2-(2-methyl-allyloxy)-benzoate (4.18 g) as white powder. $^1$H-NMR (400 MHz, D$_2$O): 7.36 (m, 2 arom. H); 7.04 (m, 2 arom. H); 5.09, 5.01 (2 d-like, C(CH$_3$)=CH$_2$); 4.57 (d-like, CH$_2$—C(CH$_3$)=CH$_2$); 1.80 C(CH$_3$)=CH$_2$). $^{13}$C-NMR (100 MHz, D$_2$O): 176.51 (C=O); 154.32; 141.73; 129.94; 129.76; 127.84; 121.03; 113.98; 112.19; 72.09; 18.57.

Example 17

Preparation of
2-Allyloxy-4-(2-hydroxy-ethoxy)-benzoic acid
(Compound 16)

The reaction of methyl 2-hydroxy-4-(2-hydroxy-ethoxy)-benzoate and allyl bromide in 2-butanone in the presence of potassium carbonate was performed as described in Example 2 to give 2-Allyloxy-4-(2-hydroxy-ethoxy)-benzoic acid as white powder. $^1$H-NMR (400 MHz, d6-DMSO): 12.12 (s, —CO$_2$H); 7.65 (d, J=8.7, 1 arom. H); 6.55 (m, 2 arom. H); 5.97 (m, —CH=CH$_2$); 5.48, 5.21 (2 d-like, CH=CH$_2$); 4.84 (m, CH$_2$CH$_2$OH); 4.58 (d-like, CH$_2$—CH=CH$_2$); 3.99, 3.67 (2t, J=4.8, CH$_2$CH$_2$OH). $^{13}$C-NMR (100 MHz, d6-DMSO): 166.45 (C=O); 162.93; 159.39; 133.30; 133.24; 116.86; 112.86; 105.84; 100.43; 69.82; 68.58; 59.40.

Example 18

Preparation of 5-Acetyl-2-allyloxy-benzoic acid
(Compound 17)

The reaction of methyl 5-acetyl-2-hydroxyl-benzoate and allyl bromide in 2-butanone in the presence of potassium carbonate was performed as described in Example 2 to give 5-Acetyl-2-allyloxy-benzoic acid as white powder. $^1$H-NMR (400 MHz, d6-DMSO): 12.94 (s, —CO$_2$H); 8.21 (m, 1 arom. H); 8.06 (m, 1 arom. H); 7.20 (m, 1 arom. H); 6.02 (m, —CH=CH$_2$); 5.50, 5.28 (2 d-like, CH=CH$_2$); 4.73 (d-like, CH$_2$—CH=CH$_2$); 2.53 (s, CH$_3$C=O). $^{13}$C-NMR (100 MHz, d6-DMSO): 195.91 (CH$_3$C=O); 166.71 (C(OH)=O); 160.44; 133.22; 132.76; 131.12; 129.11; 121.46; 117.30; 113.35; 69.81; 26.42.

Example 19

Preparation of 2-Allyloxy-5-bromo-benzoic acid
(Compound 18)

The reaction of methyl 5-bromo-2-hydroxyl-benzoate and allyl bromide in 2-butanone in the presence of potassium carbonate was performed as described in Example 2 to give 2-Allyloxy-5-bromo-benzoic acid as white powder. $^1$H-NMR (400 MHz, d6-DMSO): 12.98 (s, —CO$_2$H); 7.73 (m, 1arom. H); 7.62 (m, 1 arom. H); 7.07 (m, 1 arom. H); 5.99 (m, —CH=CH$_2$); 5.47, 5.25 (2 d-like, CH=CH$_2$); 4.62 (d-like, CH$_2$—CH=CH$_2$). $^{13}$C-NMR (100 MHz, d6-DMSO): 165.99 (C=O); 156.10; 135.10; 133.00; 132.65; 123.86; 117.15; 116.12; 111.34; 68.84.

Example 20

Preparation of 2-Allyloxy-5-chloro-benzoic acid
(Compound 19)

The reaction of methyl 5-chloro-2-hydroxyl-benzoate and allyl bromide in 2-butanone in the presence of potassium carbonate was performed as described in Example 2 to give 2-Allyloxy-5-chloro-benzoic acid as white powder. $^1$H-NMR (400 MHz, d6-DMSO): 12.96 (s, —CO$_2$H); 7.61 (m, 1 arom. H); 7.52 (m, 1 arom. H); 7.12 (m, 1 arom. H); 5.99 (m, —CH=CH$_2$); 5.47, 5.23 (2 d-like, CH=CH$_2$); 4.62 (d-like, CH$_2$—CH=CH$_2$). $^{13}$C-NMR (100 MHz, d6-DMSO): 166.08 (C=O); 155.70; 133.02; 132.25; 129.84; 123.85; 123.36; 117.15; 115.70; 68.91.

Example 21

Preparation of 4-(2-Methyl-allyloxy)-benzoic acid
(Compound 20)

The reaction of Ethyl 4-hydroxyl-benzoate and 3-Bromo-2-methyl-propene in 2-butanone in the presence of potassium carbonate was performed as described in Example 2 to give 4-(2-Methyl-allyloxy)-benzoic acid as white powder. $^1$H-NMR (400 MHz, d6-DMSO):12.59 (s, —CO$_2$H); 7.86 (d-like, J=8.0, 2 arom. H); 7.02 (d-like, J=8.0, 2 arom. H); 5.04, 4.96 (2 s, —C(CH$_3$)=CH$_2$); 4.53 (s, CH$_2$—C(CH$_3$)=CH$_2$); 1.72 (s, C(CH$_3$)=CH$_2$). $^{13}$C-NMR (100 MHz, d6-DMSO): 166.93 (—C=O); 161.87; 140.39; 131.27 (2 arom. C); 123.05; 114.42 (2 arom. C); 112.52; 70.97; 19.12.

Example 22

Preparation of 3-(2-Methyl-allyloxy)-benzoic acid
(Compound 21)

The reaction of Ethyl 3-hydroxyl-benzoate and 3-Bromo-2-methyl-propene in 2-butanone in the presence of potassium carbonate was performed as described in Example 2 to give 3-(2-Methyl-allyloxy)-benzoic acid as white powder. $^1$H-NMR (400 MHz, d6-DMSO): 7.50 (m, 1 arom. H); 7.44 (m, 2 arom. H); 7.19 (m, 1 arom. H); 5.04, 4.96 (2 s, —C(CH$_3$)=CH$_2$); 4.50 (s, CH$_2$—C(CH$_3$)=CH$_2$); 1.75 (s, C(CH$_3$)=CH$_2$). $^{13}$C-NMR (100 MHz, d6-DMSO): 166.93 (—C=O); 158.23; 140.62; 132.14; 129.67; 121.67; 119.53; 114.88; 112.33; 70.95; 19.13.

Example 23

Preparation of 3-Allyloxy-4-methoxy-benzoic acid
(Compound 22)

The reaction of methyl 3-hydroxyl-4-methoxybenzoate and allyl bromide in 2-butanone in the presence of potassium carbonate was performed as described in Example 2 to give 3-Allyloxy-4-methoxy-benzoic acid as white powder. $^1$H-NMR (400 MHz, d6-DMSO): 12.63 (s, —CO$_2$H); 7.54 (d-like, 1 arom. H); 7.43 (m, 1 arom. H); 7.04 (m, 1 arom. H); 6.02 (m, —CH=CH$_2$); 5.39, 5.23 (2 d-like, CH=CH$_2$); 4.57 (d-like, CH$_2$—CH=CH$_2$); 3.81 (s, OCH$_3$). $^{13}$C-NMR (100 MHz, d6-DMSO): 167.04 (—C=O); 152.87; 147.07; 133.59; 123.40; 122.86; 117.60; 113.62; 111.23; 68.88; 55.69.

Example 24

Preparation of
4-Methoxy-3-(2-methyl-allyloxy)-benzoic acid
(Compound 23)

The reaction of methyl 3-hydroxyl-4-methoxybenzoate and 3-Bromo-2-methyl-propene in 2-butanone in the presence of potassium carbonate was performed as described in Example 2 to give 4-Methoxy-3-(2-methyl-allyloxy)-benzoic acid as white powder. $^1$H-NMR (400 MHz, d6-DMSO): 12.63 (s, —CO$_2$H); 7.56 (d-like, 1 arom. H); 7.43 (m, 1 arom. H); 7.04 (m, 1 arom. H); 5.04, 4.90 (2 s, —C(CH$_3$)=CH$_2$); 4.48 (s, CH$_2$—C(CH$_3$)=CH$_2$); 3.79 (s, OCH$_3$); 1.75 (s, C(CH$_3$)=CH$_2$). $^{13}$C-NMR (100 MHz, d6-DMSO): 167.02 (—C=O); 152.90; 147.18; 140.76; 123.39; 122.84; 113.76; 112.33; 111.28; 71.56; 55.75; 19.16.

Example 25

Oral delivery of Insulin to Male Sprague-Dawley Rats

Insulin stock solution (15 mg/ml) (Human zinc insulin, Calbiochem-Novabiochem Corp., La Jolla, Calif.) was prepared with deionized water. Oral dosing compositions containing 200 mg/kg of a delivery agent compound of the present invention and 0.5 mg/kg of insulin in an aqueous solution were prepared for the compounds prepared in Examples 2-24.

One ml of the dosing solution was administered to fasted male Sprague-Dawley rats by oral gavage with an average weight of about 225-250 grams Blood glucose levels were then determined by glucometer (One Touch Ultra®, LifeScan, Inc.) and compared to vehicle control (1 ml/kg of water). Samples were collected prior to dosing (time 0) and at 15, 30, 45 and 60 minutes after dosing. The % glucose reduction is shown below in Table 1. The values correspond to the C minimum, and are an average % reduction with respect to the number of times the experiment was run for each delivery agent.

TABLE 1

Percent Change in Glucose

| Compound No. | Glucose (Absolute change from Control) | # of Experiments |
|---|---|---|
| 1 | −35.1% | 4 |
| 2 | −42.4% | 2 |
| 3 | −25.5% | 3 |
| 4 | −41.6% | 3 |
| 5 | −40.8% | 3 |
| 6 | −42.8% | 3 |
| 7 | −38.8% | 2 |
| 8 | −31.6% | 1 |
| 9 | −27.8% | 1 |
| 10 | −27.2% | 1 |
| 11 | −24.0% | 1 |
| 12 | −13.5% | 1 |
| 13 | −30.7% | 1 |
| 14 | −14.4% | 2 |
| 15 | −37.4% | 2 |
| 16 | −4.6% | 1 |
| 17 | 0.6% | 1 |
| 18 | −5.0% | 1 |
| 19 | −21.5% | 1 |
| 20 | −51.1% | 3 |
| 21 | −27.4% | 1 |
| 22 | −10.2% | 1 |
| 23 | −8.4% | 1 |

Insulin dosing solutions were also prepared as shown in Table 2. The solutions were administered to fasted male Sprague-Dawley rats and the % glucose reduction was determined in the same manner as described above.

TABLE 2

Insulin Dose Titrations of Delivery Agent Compounds

| Compound No. | Insulin Dose (mg/kg) | Carrier Dose (mg/kg) | Glucose (Absolute change from Control) |
|---|---|---|---|
| 1 | 0.25 | 200 | 3.0% |
| 1 | 0 | 200 | −12.5% |
| 1 | 0.25 | 100 | −17.9% |
| 4 | 0.25 | 200 | −11.4% |
| 4 | 0 | 200 | 8.8% |
| 5 | 0.25 | 200 | −5.4% |
| 5 | 0 | 200 | −6.3% |
| 6 | 0.25 | 200 | −18.2% |
| 6 | 0 | 200 | −10.7% |
| 20 | 0.25 | 200 | −13.6% |
| 20 | 0 | 200 | −14.5% |
| 20 | 0.25 | 200 | −54.8% |
| 20 | 0 | 200 | −31.0% |

Example 26

The compounds of Formula II are synthesized according to Scheme 2 by the coupling reaction of the corresponding ethyl hydroxy-benzoate and bromide.

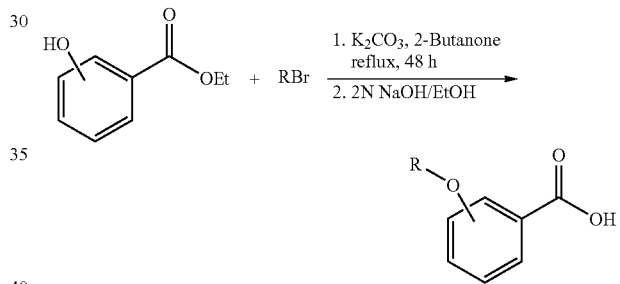

Scheme 2

Example 27

3-Propoxy-benzoic acid (Compound 24)

Under N$_2$, the mixture of ethyl 3-hydroxybenzoate (4.16 g, 25 mmol), propyl bromide (4.31 g, 3.2 ml, 35 mmol) and potassium carbonate (4.15 g, 30 mmol) in dry 2-butanone (100 ml) was heated to reflux for 48 h. After the reaction mixture cooled down to 25° C., the suspended inorganic salt was removed by filtration. The concentration of the resulting solution by rotary evaporation yielded pale yellowish syrup, which was then mixed with 2N NaOH (18 ml, 36 mmol) and EtOH (30 ml). After this mixture was stirred for 2 h at 50° C., ethanol was removed at reduced pressure. The aqueous solution was acidified by 6N HCl to pH 2 at 5° C. to generate white precipitate, which was then collected by filtration. The recrystallization of this crude product from hexane/ether yielded pure 3-Propoxy-benzoic acid as colorless crystal (3.77 g, 83.7%). $^1$H-NMR (400 MHz, d6-DMSO): 7.43 (m, 1 arom. H); 7.34 (m, 2 arom. H); 7.08 (m, 1 arom. H); 3.88 (t, CH$_3$CH$_2$CH$_2$O); 1.65 (m, CH$_3$CH$_2$CH$_2$O); 0.88 (t, CH$_3$CH$_2$CH$_2$O). $^{13}$C-NMR (100 MHz, d6-DMSO): 167.12 (—C=O); 158.63; 132.12; 129.68; 121.41; 119.33; 114.41; 69.09; 21.95; 10.32.

Example 28

4-Propoxy-benzoic acid (Compound 25)

The reaction of propyl bromide and ethyl 4-hydroxybenzoate in the presence of potassium carbonate was performed as described for Compound 24 to give 4-Propoxy-benzoic acid as white powder. $^1$H-NMR (400 MHz, d6-DMSO): 12.58 (s, COOH); 7.86 (d, J=8.8, 2 arom. H); 6.97 (d, J=8.8, 2 arom. H); 3.97 (t, CH$_3$CH$_2$CH$_2$O); 1.72 (m, CH$_3$CH$_2$CH$_2$O); 0.96 (t, CH$_3$CH$_2$CH$_2$O). $^{13}$C-NMR (100 MHz, d6-DMSO): 166.99 (—C=O); 162.29; 131.33 (2 arom. C); 122.78; 114.18 (2 arom. C); 69.21; 21.90; 10.30.

Example 29

2-Propoxy-benzoic acid (Compound 26)

The reaction of propyl bromide and ethyl salicylate in the presence of potassium carbonate was performed as described for Compound 24 to give 2-Propoxy-benzoic acid as white powder. $^1$H-NMR (400 MHz, d6-DMSO): 12.56 (s, COOH); 7.61 (m, 1 arom. H); 7.45 (m, 1 arom. H); 7.07 (m, 1 arom. H); 6.96 (m, 1 arom. H); 3.96 (t, CH$_3$CH$_2$CH$_2$O); 1.71 (m, CH$_3$CH$_2$CH$_2$O); 0.96 (t, CH$_3$CH$_2$CH$_2$O). $^{13}$C-NMR (100 MHz, d6-DMSO): 167.49 (—C=O); 157.41; 132.82; 130.51; 121.73; 119.91; 113.35; 69.63; 22.04; 10.39.

Example 30

3-Butoxy-benzoic acid (Compound 27)

The reaction of butyl bromide and ethyl 3-hydroxybenzoate in the presence of potassium carbonate was performed as described for Compound 24 to give 3-butoxy-benzoic acid as white powder. $^1$H-NMR (400 MHz, d6-DMSO): 12.93 (s, COOH); 7.48 (m, 1 arom. H); 7.40 (m, 2 arom. H); 7.12 (m, 1 arom. H); 3.97 (t, CH$_3$CH$_2$CH$_2$CH$_2$O); 1.69 (m, CH$_3$CH$_2$CH$_2$CH$_2$O); 1.42 (m, CH$_3$CH$_2$CH$_2$CH$_2$O); 0.91 (t, CH$_3$CH$_2$CH$_2$CH$_2$O). $^{13}$C-NMR (100 MHz, d6-DMSO): 167.12 (—C=O); 158.63; 132.13; 129.67; 121.40; 119.31; 114.41; 67.30; 30.64; 18.68; 13.65.

Example 31

4-Butoxy-benzoic acid (Compound 28)

The reaction of butyl bromide and ethyl 4-hydroxybenzoate in the presence of potassium carbonate was performed as described for Compound 24 to give 4-butoxy-benzoic acid as white powder. $^1$H-NMR (400 MHz, d6-DMSO): 12.57 (s, COOH); 7.85 (d, J=8.8, 2 arom. H); 6.98 (d, J=8.8, 2 arom. H); 4.02 (t, CH$_3$CH$_2$CH$_2$CH$_2$O); 1.69 (m, CH$_3$CH$_2$CH$_2$CH$_2$O); 1.43 (m, CH$_3$CH$_2$CH$_2$CH$_2$O); 0.92 (t, CH$_3$CH$_2$CH$_2$CH$_2$O). $^{13}$C-NMR (100 MHz, d6-DMSO): 166.99 (—C=O); 162.29; 131.32 (2 arom. C); 122.77; 114.17 (2 arom. C); 67.45; 30.58; 18.66; 13.63.

Example 32

2-Butoxy-benzoic acid (Compound 29)

Under N$_2$, the mixture of ethyl salicylate (4.16 g, 25 mmol), butyl bromide (4.80 g, 3.77 ml, 35 mmol) and potassium carbonate (4.15 g, 30 mmol) in dry 2-Butanone (100 ml) was heated to reflux for 48 h. After the reaction mixture cooled down to 25° C., the suspended inorganic salt was removed by filtration. The concentration of the resulting solution by rotary evaporation yielded pale yellowish syrup, which was then mixed with 2N NaOH (18 ml, 36 mmol) and EtOH (30 ml). After this mixture was stirred for 2 h at 50° C., ethanol was removed at reduced pressure. After the aqueous solution was acidified by 6N HCl to pH 2 at 5° C., the mixture was extracted with Et$_2$O (50 ml×3). The organic phase was combined and washed with water (10 ml×2) respectively. The ether extract was dried with anhydrous sodium sulfate and then concentrated to give 2-Butoxy-benzoic acid as oil (3.40 g, 17.5 mmol), which was then treated with of 1M sodium trimethylsilanolate (17.0 ml, 17.0 mmol) to give Sodium 2-allyloxy-6-methyl-benzoate (3.53 g, 65.3%) as white powder. $^1$H-NMR (400 MHz, D$_2$O): 7.22 (m, 2 arom. H); 6.93 (m, 2 arom. H); 3.94 (t, CH$_3$CH$_2$CH$_2$CH$_2$O); 1.59 (m, CH$_3$CH$_2$CH$_2$CH$_2$O); 1.32 (m, CH$_3$CH$_2$CH$_2$CH$_2$O); 0.78 (t, CH$_3$CH$_2$CH$_2$CH$_2$O). $^{13}$C-NMR (100 MHz, D$_2$O): 176.54 (—C=O); 154.93; 130.10; 129.81; 127.85; 120.82; 114.13; 69.26; 30.64; 18.68; 13.21.

Example 33

4-Isobutoxy-benzoic acid (Compound 30)

The reaction of isobutyl bromide and ethyl 4-hydroxybenzoate in the presence of potassium carbonate was performed as described for Compound 24 to give 4-isobutoxy-benzoic acid as white powder. $^1$H-NMR (400 MHz, d6-DMSO): 12.56 (s, COOH); 7.85 (d, J=8.8, 2 arom. H); 6.98 (d, J=8.8, 2 atom. H); 3.80 (d, J=6.4, (CH$_3$)$_2$CHCH$_2$O); 2.01 (m, (CH$_3$)$_2$CHCH$_2$O); 0.96 (d, J=6.4, (CH$_3$)$_2$CHCH$_2$O). $^{13}$C-NMR (100 MHz, d6-DMSO): 166.97 (—C=O); 162.35; 131.32 (2 arom. C); 122.78; 114.22 (2 arom. C); 73.89; 27.60; 18.94.

Example 34

3-Isobutoxy-benzoic acid (Compound 31)

The reaction of isobutyl bromide and ethyl 3-hydroxybenzoate in the presence of potassium carbonate was performed as described for Compound 24 to give 3-isobutoxy-benzoic acid as white powder. $^1$H-NMR (400 MHz, d6-DMSO): 12.94 (s, COOH); 7.48 (m, 1 arom. H); 7.40 (m, 2 arom. H); 7.12 (m, 1 arom. H); 3.76 (d, J=6.4, (CH$_3$)$_2$CHCH$_2$O); 2.00 (m, (CH$_3$)$_2$CHCH$_2$O); 0.96 (d, J=6.4, (CH$_3$)$_2$CHCH$_2$O). $^{13}$C-NMR (100 MHz, d6-DMSO): 167.11 (—C=O); 158.73; 132.12; 129.68; 121.42; 119.35; 114.46; 73.46; 27.66; 18.98 (2 C).

Example 35

Oral delivery of Insulin to Male Sprague-Dawley Rats

Insulin stock solution (15 mg/ml) (Human zinc insulin, Calbiochem-Novabiochem Corp., La Jolla, Calif.) was prepared with deionized water. Oral dosing compositions containing 200 mg/kg of a delivery agent compound of the present invention and 0.5 mg/kg of insulin in an aqueous solution were prepared for the compounds prepared in Examples 27-34. One ml of the dosing solution was administered to fasted male Sprague-Dawley rats by oral gavage with an average weight of about 225-250 grams. Blood glucose levels were then determined by glucometer (One Touch Ultra®, LifeScan, Inc.) and compared to vehicle control (1 ml/kg of water). Samples were collected prior to dosing (time 0) and at 15, 30, 45 and 60 minutes after dosing. The % glucose reduction is shown below in Table 3. The values correspond to the C minimum, and are an average % reduction with respect to the number of times the experiment was run for each delivery agent.

TABLE 3

Percent Change in Glucose

| Compound No. | Glucose (Absolute change from Control) | # of Experiments |
|---|---|---|
| 24 | −15.2 | 2 |
| 25 | −25.5 | 2 |
| 26 | −14.2 | 1 |
| 27 | −23.9 | 1 |
| 28 | −22.3 | 1 |
| 29 | −34.9 | 1 |
| 30 | −29.8 | 1 |
| 31 | −9.5 | 2 |

Example 36

The compounds of Formula III were synthesized according to Scheme 3 by the coupling reaction of the corresponding alcohol and bromomethyl benzoic acid. R is methyl, ethyl, isopropyl, propyl, butyl, allyl, 1-methylallyl, 2-methylallyl, or butenyl.

Scheme 3

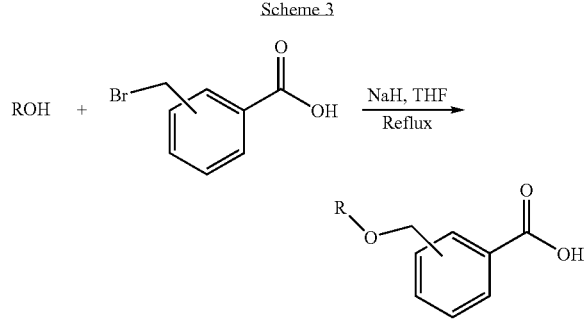

Example 37

4-But-3-enyloxymethyl-benzoic acid (Compound 33)

To the suspension of sodium hydride (1.390 g, 95%, 55 mmol) in tetrahydrofuran (150 ml), But-3-en-1-ol (3.966 g, 4.7 ml, 55 mmol) was added. After the reaction mixture was refluxed for 30 min, 4-Bromomethyl-benzoic acid (5.376 g, 25 mmol) was added and the reaction was kept to reflux for additional 10 h. After cooling down, water (100 ml) was added and the tetrahydrofuran was removed under vacuum. This resulting aqueous solution was adjusted with 6N HCl to pH 2 at 5° C. to generate white precipitate, which was then collected by filtration. The recrystallization of this crude product from hexane/ether yielded pure 4-But-3-enyloxymethyl-benzoic acid as colorless crystal (4.15 g, 80.5%). $^1$H-NMR (400 MHz, d6-DMSO): 7.91 (d, J=8.2, 2 arom. H); 7.41 (J=8, 2 arom. H); 5.81 (m, —CH═CH$_2$); 5.10 (2 d-like, —CH═CH$_2$); 4.53 (s, —OCH$_2$—C$_6$H$_4$); 3.49 (m, CH$_2$═CH—CH$_2$CH$_2$O); 2.32 (m, CH$_2$═CH—CH$_2$CH$_2$O). $^{13}$C-NMR (100 MHz, d6-DMSO): 167.14 (—C═O); 143.72; 135.49; 129.73; 129.28 (2 arom. C); 127.08 (2 arom. C); 116.46; 71.13; 69.18.

Example 38

4-Allyloxymethyl-benzoic acid (Compound 32)

The reaction of allyl alcohol and 4-Bromomethyl-benzoic acid in the presence of sodium hydride was performed as described for Compound 33 to give 4-Allyloxymethyl-benzoic acid as white powder. $^1$H-NMR (400 MHz, d6-DMSO): 7.91 (d, J=8.3, 2 arom. H); 7.42 (d, J=8.3, 2 arom.H); 5.90 (m, —CHCH$_2$); 5.30, 5.18 (2 d-like, —CH═CH$_2$); 4.54 (s, —OCH$_2$—C$_6$H$_4$); 4.01 (2 d-like, CH$_2$═CHCH$_2$O). $^{13}$C-NMR (100 MHz, d6-DMSO): 161.18 (—C═O); 143.48; 134.97; 129.95; 129.31 (2 arom.C); 127.11 (2 arom.C); 116.63; 70.64 (2 C).

Example 39

4-(1-Methyl-allyloxymethyl)-benzoic acid (Compound 34)

The reaction of But-3-en-2-ol and 4-Bromomethyl-benzoic acid in the presence of sodium hydride was performed as described for Compound 33 to give 4-(1-Methyl-allyloxymethyl)-benzoic acid as white powder. $^1$H-NMR (400 MHz, d6-DMSO): 12.89 (S, COOH); 7.90 (d, J=8.3, 2 arom. H); 7.42 (d, J=8.3, 2 arom.H); 5.77 (m, —CH═CH$_2$); 5.21, 5.16 (2 d-like, —CH═CH$_2$); 4.54, 4.44 (AB, J=8.9, —OCH$_2$—C$_6$H$_4$); 3.95 (m, CH(CH$_3$)O); 1.22 (d, CH(CH$_3$)O). $^{13}$C-NMR (100 MHz, d6-DMSO): 167.14 (—C═O); 144.00; 140.10; 129.65; 129.27 (2 arom.C); 1267.00 (2 arom.C); 116.06; 75.83; 68.56; 20.97.

Example 40

4-(2-Methyl-allyloxymethyl)-benzoic acid (Compound 35)

The reaction of 2-Methyl-prop-2-en-1-ol and 4-Bromomethyl-benzoic acid in the presence of sodium hydride was performed as described for Compound 33 to give 4-(2-Methyl-allyloxymethyl)benzoic acid as white powder. $^1$H-NMR (400 MHz, d6-DMSO): 12.85 (S, COOH); 7.91 (d, J=8.3, 2 arom. H); 7.42 (d, J=8.3, 2 arom.H); 4.96, 4.88 (2 s-like; C═CH$_2$); 4.51 (s, —OCH$_2$—C$_6$H$_4$); 3.90 (s, CH$_2$O); 1.69 (s, CH$_3$). $^{13}$C-NMR (100 MHz, d6-DMSO): 167.12 (—C═O); 143.60; 141.98; 129.74; 129.32 (2 arom.C); 127.09 (2 arom.C); 111.74; 73.50; 70.52; 19.29.

Example 41

3-(2-Methyl-allyloxymethyl)-benzoic acid (Compound 37)

To the suspension of Sodium Hydride (1.516 g, 95%, 60 mmol) in tetrahydrofuran (150 ml), 2-Methyl-prop-2-en-1-ol (4.323 g, 4.1 ml, 60 mmol) was added. After the reaction mixture was refluxed for 30 min, 3-Chloromethyl-benzoic acid (4.10 g, 24 mmol) was added and the reaction was kept to reflux for additional 10 h. After cooling down, water (100 ml) was added and the tetrahydrofuran was removed under vacuum. This resulting aqueous solution was adjusted with 6N HCl to pH 2 at 5° C., and the mixture was extracted with Et$_2$O (50 ml×3). The organic phase was combined and washed with water (10 ml×2) respectively. The ether extract was dried with anhydrous sodium sulfate and then concentrated to give 3-(2-Methyl-allyloxymethyl)-benzoic acid as colorless oil (4.25 g, 85.9%). $^1$H-NMR (400 MHz, d6-DMSO): 7.90 (m, 1 arom.H); 7.85 (m, 1 arom.H); 7.55 (m, 1 arom.H); 7.45 (m, 1 arom.H); 4.96, 4.88 (2 s-like; C=$CH_2$); 4.50 (s, —$OCH_2$—$C_6H_4$); 3.90 (s, $CH_2O$); 1.69 (s, $CH_3$). $^{13}$C-NMR (100 MHz, d6-DMSO): 167.22 (—C=O); 142.03; 139.00; 131.72; 130.78; 128.56; 128.31; 128.07; 111.71; 73.41; 70.58; 19.30.

Example 42

3-Allyloxymethyl-benzoic acid (Compound 38)

The reaction of allyl alcohol and 3-chloromethyl-benzoic acid in the presence of sodium hydride was performed as described for Compound 37 to give 3-Allyloxymethyl-benzoic acid as colorless oil. $^1$H-NMR (400 MHz, d6-DMSO): 7.90 (m, 1 arom.H); 7.85 (m, 1 arom.H); 7.55 (m, 1 arom.H); 7.47 (m, 1 arom.H); 5.92 (m, —CH=$CH_2$); 5.30, 5.16 (2 d-like, —CH=$CH_2$); 4.52 (s, —$OCH_2$—$C_6H_4$); 4.00 (d-like, $CH_2$=$CHCH_2$O). $^{13}$C-NMR (100 MHz, d6-DMSO): 167.24 (—C=O); 138.98; 135.04; 131.77; 130.80; 128.56; 128.34; 128.14; 116.60; 70.70; 70.55.

Example 43

3-But-3-enyloxymethyl-benzoic acid (Compound 36)

The reaction of But-3-en-1-ol and 3-chloromethyl-benzoic acid in the presence of sodium hydride was performed as described for Compound 37 to give 3-But-3-enyloxymethyl-benzoic acid as colorless oil. $^1$H-NMR (400 MHz, d6-DMSO): 7.89 (m, 1 arom.H); 7.84 (m, 1 arom.H); 7.54 (m, 1 arom.H); 7.47 (m, 1 arom.H); 5.80 (m, —CH=$CH_2$); 5.06 (2 d-like, —CH=$CH_2$); 4.61 (s, —$OCH_2$—$C_6H_4$); 3.49 (m, $CH_2$—CH—$CH_2CH_2$O); 2.31 (m, $CH_2$=CH—$CH_2CH_2$O). $^{13}$C-NMR (100 MHz, d6-DMSO): 167.14 (—C=O); 139.11; 135.52; 131.72; 130.76; 128.54; 128.27; 128.10; 126.44; 71.17; 69.06; 33.70.

Example 44

4-Ethoxymethyl-benzoic acid (Compound 39)

The reaction of ethanol and 4-Bromomethyl-benzoic acid in the presence of sodium hydride was performed as described for Compound 33 to give 4-Ethoxymethyl-benzoic acid as white powder. $^1$H-NMR (400 MHz, d6-DMSO): 7.89 (d, J=8.2, 2 arom.H); 7.40 (d, J=8.2, 2 arom.H); 4.50 (s, $OCH_2C_6H_4$); 3.49 (q, J=6.9, $CH_3CH_2$); 1.15 (t, J=6.9, $CH_3CH_2$). $^{13}$C-NMR (100 MHz, d6-DMSO): 167.24 (—C=O); 143.88; 129.65; 129.28 (2 arom. C); 127.05 (2 arom. C); 70.95; 65.25; 15.06.

Example 45

4-Isopropoxymethyl-benzoic acid (Compound 40)

The reaction of isopropanol and 4-Bromomethyl-benzoic acid in the presence of sodium hydride was performed as described for Compound 33 to give 4-Isopropoxymethyl-benzoic acid as white powder. $^1$H-NMR (400 MHz, d6-DMSO): 7.89 (d, J=8.2, 2 arom.H); 7.41 (d, J=8.2, 2 arom.H); 4.51 (s, $OCH_2C_6H_4$—); 3.63 (m, $CH(CH_3)_2$); 1.14 (d, $CH(CH_3)_2$). $^{13}$C-NMR (100 MHz, d6-DMSO): 167.24 (—C=O); 144.47; 129.52; 129.23 (2 arom.C); 126.93 (2 arom. C); 70.67; 68.47; 22.00 (2 C).

Example 46

4-Propoxymethyl-benzoic acid (Compound 41)

The reaction of propanol and 4-Bromomethyl-benzoic acid in the presence of sodium hydride was performed as described for Compound 33 to give 4-propoxymethyl-benzoic acid as white powder. $^1$H-NMR (400 MHz, d6-DMSO): 7.89 (d, J=8.2, 2 arom.H); 7.40 (d, J=8.2, 2 arom.H); 4.50 (s, $OCH_2C_6H_4$—); 3.38 (t, $CH_3CH_2CH_2O$); 1.54 (m, $CH_3CH_2CH_2O$); 0.87 (t, $CH_3CH_2CH_2O$).). $^{13}$C-NMR (100 MHz, d6-DMSO): 167.24 (—C=O); 143.94; 129.67; 129.30 (2 arom. C); 127.03 (2 arom. C); 71.53; 71.13; 22.43; 10.55.

Example 47

3-Ethoxymethyl-benzoic acid (Compound 42)

The reaction of ethanol and 3-Chloromethyl-benzoic acid in the presence of sodium hydride was performed as described for Compound 33 to give 3-ethoxymethyl-benzoic acid as white powder. $^1$H-NMR (400 MHz, d6-DMSO): 7.89 (m, 1 arom.H); 7.84 (m, 1 arom.H); 7.54 (m, 1 arom.H); 7.46 (m, 1 arom.H); 4.49 (s, $OCH_2C_6H_4$—); 3.48 (q, J=6.9, $CH_3CH_2$); 1.15 (t, J=6.9, $CH_3CH_2$). $^{13}$C-NMR (100 MHz, d6-DMSO): 167.24 (—C=O); 139.26; 131.67; 130.76; 128.51; 128.23; 128.06; 71.01; 65.14; 15.07.

Example 48

3-Isopropoxymethyl-benzoic acid (Compound 43)

The reaction of isopropanol and 3-Chloromethyl-benzoic acid in the presence of sodium hydride was performed as described for Compound 33 to give 3-isopropoxymethyl-benzoic acid as white powder. $^1$H-NMR (400 MHz, d6-DMSO): 7.89 (m, 1 arom.H); 7.84 (m, 1 arom.H); 7.54 (m, 1 arom.H); 7.46 (m, 1 arom.H); 4.49 (s, $OCH_2C_6H_4$—); 3.653 (m, $CH(CH_3)_2$); 1.14 (d, $CH(CH_3)_2$). $^{13}$C-NMR (100 MHz, d6-DMSO): 167.24 (—C=O); 139.79; 131.56; 130.68; 128.43; 128.08; 127.92; 70.54; 68.50; 22.02 (2 C).

Example 49

3-Propoxymethyl-benzoic acid (Compound 44)

The reaction of propanol and 3-Chloromethyl-benzoic acid in the presence of sodium hydride was performed as described for Compound 33 to give 3-propoxymethyl-benzoic acid as white powder. $^1$H-NMR (400 MHz, d6-DMSO): 7.89 (m, 1 arom.H); 7.84 (m, 1 arom.H); 7.53 (m, 1 arom.H); 7.46 (m, 1 arom.H); 4.50 (s, $OCH_2C_6H_4$—); 3.38 (t, $CH_3CH_2CH_2O$); 1.54 (m, $CH_3CH_2CH_2O$); 0.87 (t, $CH_3CH_2CH_2O$). $^{13}$C-NMR (100 MHz, d6-DMSO): 167.25 (—C=O); 139.31; 131.63; 130.77; 128.51; 128.22; 128.01; 71.40; 71.16; 22.43; 10.56.

Example 50

Oral delivery of Insulin to Male Sprague-Dawley Rats

Insulin stock solution (15 mg/ml) (Human zinc insulin, Calbiochem-Novabiochem Corp., La Jolla, Calif.) was prepared with deionized water. Oral dosing compositions containing 200 mg/kg of a delivery agent compound of the present invention and 0.5 mg/kg of insulin in an aqueous solution were prepared for the compounds prepared in Examples 37-49. One ml of the dosing solution was administered to fasted male Sprague-Dawley rats by oral gavage with an average weight of about 225-250 grams. Blood glucose levels were then determined by glucometer (One Touch Ultra®, LifeScan, Inc.) and compared to vehicle control (1 ml/kg of water). Samples were collected prior to dosing (time 0) and at 15, 30, 45 and 60 minutes after dosing. The % glucose reduction is shown below in Table 5. The values correspond to the C minimum, and are an average % reduction with respect to the number of times the experiment was run for each delivery agent.

TABLE 5

Percent Change in Glucose

| Compound No. | Glucose (Absolute change from Control) | # of Experiments |
|---|---|---|
| 32 | −19.5 | 2 |
| 33 | −38.5 | 3 |
| 34 | −16.6 | 1 |
| 35 | −16.0 | 1 |
| 36 | −20.7 | 2 |
| 37 | −8.4 | 2 |
| 38 | −13.1 | 3 |
| 39 | −1.9 | 1 |
| 40 | −31.9 | 1 |
| 41 | −19.2 | 1 |
| 42 | −11.3 | 1 |
| 43 | −29.3 | 1 |
| 44 | −20.8 | 1 |

Example 51

Prophetic Examples

In addition to the embodiments previously disclosed herein, the following compositions may be prepared.

A pharmaceutical composition that includes Compound 1, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 2, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 3, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 4, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 5, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 6, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 7, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 8, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 9, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 10, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 11, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 12, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 13, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 14, or a salt thereof; and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 15, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 16, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 17, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 18, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 19, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 20, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 21, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 22, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 23, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 24, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 25, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 26, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 27, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 28, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 29, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 30, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 31, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 32, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 33, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 34, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 35, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 36, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 37, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 38, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 39, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 40, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 41, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 42, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 43, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

A pharmaceutical composition that includes Compound 44, or a salt thereof, and at least one of the following: growth hormone, insulin, heparin, calcitonin, cromolyn sodium, gallium salts, desferrioxamine, parathyroid hormone, bisphosphonates, BIBN4096BS, glucagon, GLP-1, Peptide YY (PYY); or equivalents, analogs or fragments thereof.

The above-mentioned patents, applications, test methods, and publications are hereby incorporated by reference in their entirety.

The present invention has been described in details with particular reference to some embodiments thereof, but it will be understood that many variations and modifications of the present invention suggest themselves to those skilled in the art in light of the above detailed description. All such obvious variations and modifications can be affected without departing from the spirit and scope of the appended claims of the present invention.

The invention claimed is:

1. A pharmaceutical composition comprising:
   (A) a biologically active agent selected from proteins, polypeptides, peptides, hormones, polysaccharides, mucopolysaccharides, carbohydrates, and lipids; and
   (B) at least one delivery agent compound selected from
   (i) compounds of formula I

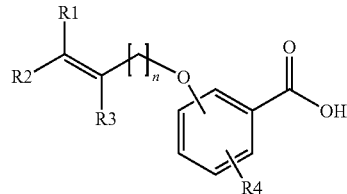

and pharmaceutically acceptable salts thereof, wherein
   n is 1, 2, 3 or 4;
   R1, R2 and R3 are independently hydrogen, methyl or halogen; and
   R4 is hydrogen, methyl, methoxy, hydroxy, halogen, acetyl, or 2-hydroxy-ethoxy; and
   (ii) compounds of formula III

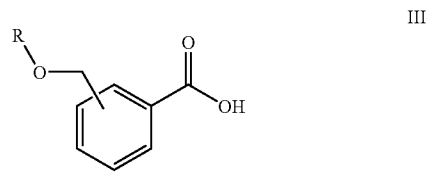

wherein R is methyl, ethyl, isopropyl, propyl, butyl, allyl, 1-methylallyl, 2-methylallyl, or butenyl.

2. The pharmaceutical composition of claim 1, wherein at least one of R1-R4 of Formula I is methyl, methoxy, hydroxy, or halogen.

3. The pharmaceutical composition of claim 2, wherein at least one of R1-R4 of Formula I is chlorine or fluorine.

4. The pharmaceutical composition of claim 1, wherein at least one of R1-R4 of Formula I is chlorine or fluorine.

5. The pharmaceutical composition of claim 1, wherein the at least one delivery agent compound is selected from the group consisting of:

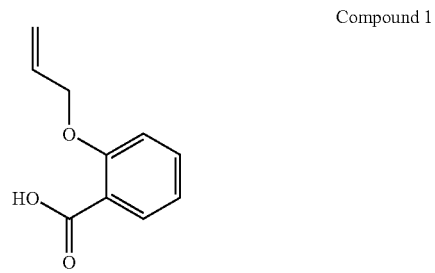

Compound 1

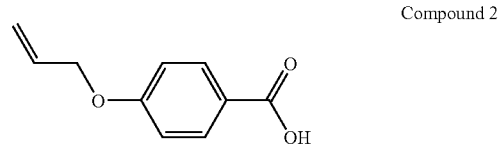

Compound 2

-continued

Compound 3

Compound 4

Compound 5

Compound 6

Compound 7

Compound 8

Compound 9

Compound 10

Compound 11

Compound 12

Compound 13

Compound 14

Compound 15

Compound 16

Compound 17

Compound 18

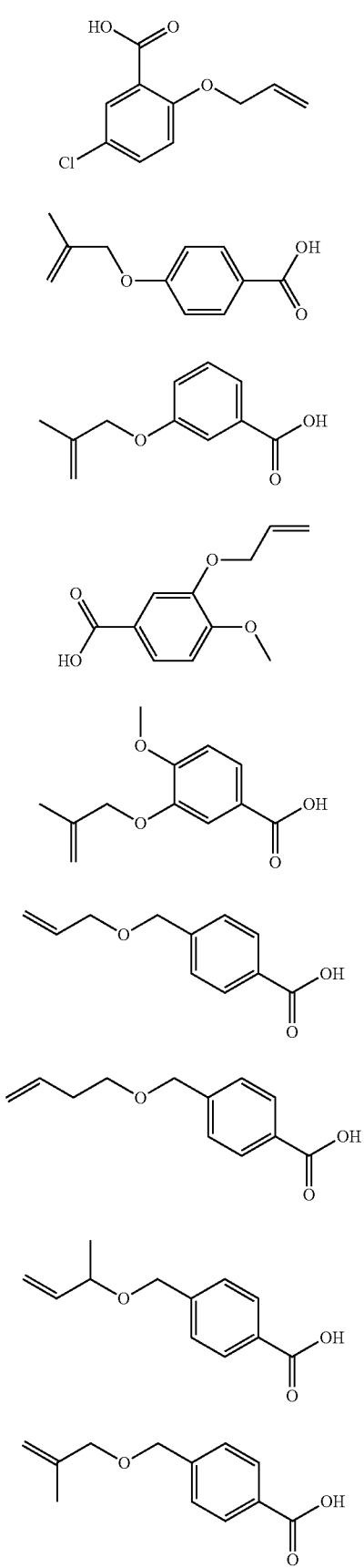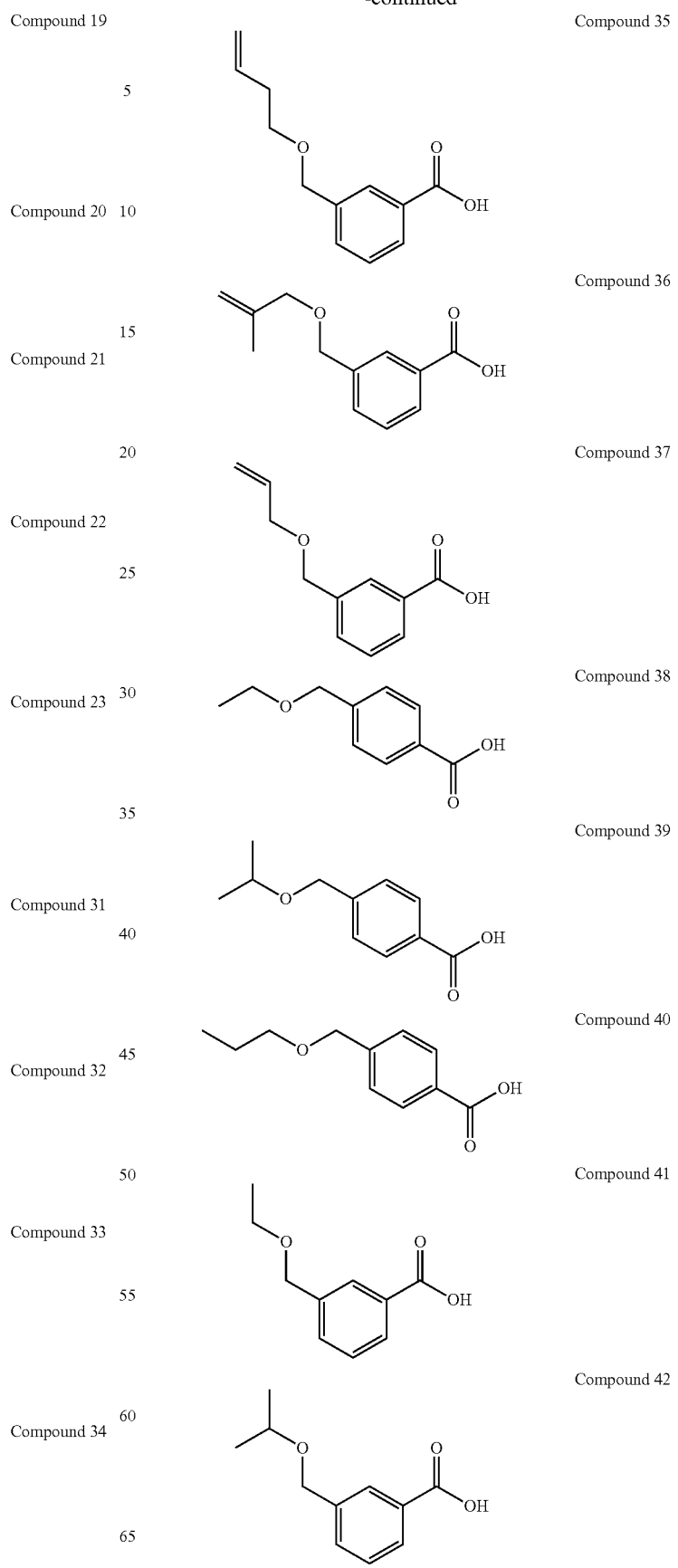

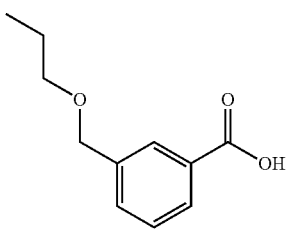

Compound 43 and pharmaceutically acceptable salts thereof.

6. The pharmaceutical composition of claim 1, wherein the biologically active agent is selected from the group consisting of: growth hormones, human growth hormones, recombinant human growth hormones, bovine growth hormones, porcine growth hormones, growth hormone releasing hormones, growth hormone releasing factor, interferons, α-interferon, β-interferon, γ-interferon, interleukin-1, interleukin2, insulin, porcine insulin, bovine insulin, human insulin, human recombinant insulin, insulin-like growth factor (IGF), IGF-I, heparin, unfractionated heparin, heparinoids, dermatans, chondroitins, low molecular weight heparin, very low molecular weight heparin, ultra low molecular weight heparin, calcitonin, salmon calcitonin, eel calcitonin, porcine calcitonin, human calcitonin, erythropoietin, atrial naturetic factor, antigens, monoclonal antibodies, somatostatin, protease inhibitors, adrenocorticotropin, gonadotropin releasing hormone, oxytocin, leutinizing-hormone-releasing hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine, bisphosphonates, alendronate, tiludronate, etidronate, clodronate, pamidronate, olpadronate, incadronate, parathyroid hormone (PTH), fragments of PTH, anti-migraine agents, sumatriptan, almotriptan, naratriptan, rizatriptan, frovatriptan, eletriptan, BIBN-4096BS, calcitonin gene-related proteins antagonists, glucagon-like peptide 1, Argatroban, glucagon, caspofungin acetate, antimicrobials, antibiotics, anti-bacterials, anti-fungal agents, vitamins, and analogs, mimetics or polyethylene glycol (PEG)-modified derivatives of these compounds, or any combination thereof.

7. The pharmaceutical composition of claim 1, wherein the biologically active agent is selected from insulin, heparin, human growth hormone, leutinizing-hormone-releasing hormone, and caspofungin acetate.

8. The pharmaceutical composition of claim 7, wherein the composition comprises about 0.1 to 2.0 mg/kg of insulin and about 50 to 800 mg/kg of the delivery agent compound, or the composition comprises about 5 to 125 mg/kg of heparin and about 5 to 500 mg/kg of the delivery agent compound, or the composition comprises about 0.25 to 10 mg/kg of recombinant human growth hormone and about 50 to 500 mg/kg of the delivery agent compound, or the composition comprises about 0.1 to 10 mg/kg of leutinizing-hormone-releasing hormone and about 50 to 500 mg/kg of the delivery agent compound, or the composition comprises about 5 to 125 mg/kg of caspofungin acetate and about 50 to 500 mg/kg of the delivery agent compound.

9. A method for administering a biologically-active agent to an animal in need of the agent, the method comprising administering orally to the animal the pharmaceutical composition of claim 1.

10. A method of treating a disease in an animal characterized by hyperglycemia, comprising administering to the animal the pharmaceutical composition of claim 1.

11. A method of treating a disease in an animal characterized by intravascular thrombi or deep vein thrombosis, comprising administering to the animal the pharmaceutical composition of claim 1, wherein the biologically active agent is heparin.

12. A method of treating or preventing short stature in a subject, comprising administering to the subject the pharmaceutical composition of claim 1, wherein the biologically active agent is recombinant human growth hormone.

13. A method of treating a disease that requires supplementation of growth hormone or leutenizing-hormone-releasing hormone, comprising administering to a subject in need thereof the pharmaceutical composition of claim 1, wherein the biologically active agent is leutenizing-hormone-releasing hormone.

14. A method of treating or preventing infertility in men or women that requires supplementation of leutenizing-hormone-releasing hormone, comprising administering to a subject in need thereof the pharmaceutical composition of claim 1, wherein the biologically active agent is leutenizing-hormone-releasing hormone.

15. A method of treating candidiasis, comprising administering to a subject in need thereof the pharmaceutical composition of claim 1, wherein the biologically active agent is caspofungin acetate.

16. A method of increasing the bioavailability of a pharmaceutical composition containing an a biologically an active agent selected from proteins, polypeptides, peptides, hormones, polysaccharides, mucopolysaccharides, carbohydrates, and lipids, comprising adding at least one delivery agent compound of claim 1 to the pharmaceutical composition.

17. A method for preparing a pharmaceutical composition of claim 1 comprising mixing:
(A) at least one biologically active agent selected from proteins, polypeptides, peptides, hormones, polysaccharides, mucopolysaccharides, carbohydrates, and lipids;
(B) at least one said delivery agent; and
(C) optionally, a dosing vehicle.

* * * * *